US006248723B1

(12) United States Patent
Irvin

(10) Patent No.: US 6,248,723 B1
(45) Date of Patent: Jun. 19, 2001

(54) METHOD FOR TREATMENT OF INFLAMMATORY DISEASE

(75) Inventor: Charles G. Irvin, Englewood, CO (US)

(73) Assignee: National Jewish Medical and Research Center, Denver, CO (US)

( * ) Notice: Subject to any disclaimer, the term of this patent is extended or adjusted under 35 U.S.C. 154(b) by 0 days.

(21) Appl. No.: 09/095,877

(22) Filed: Jun. 10, 1998

Related U.S. Application Data

(60) Provisional application No. 60/063,605, filed on Jun. 10, 1997.

(51) Int. Cl.$^7$ .......................... A61K 48/00; A61K 38/00; A61K 39/395; C07K 14/00; C12N 15/11
(52) U.S. Cl. ........................ 514/44; 514/2; 424/143.1; 435/320.1; 435/360; 435/375; 435/456; 530/350; 530/388.22; 536/23.1; 536/23.5
(58) Field of Search .............................. 424/130.1, 143.1, 424/158.1; 435/6, 7.1, 69.1, 91.1, 91.31, 440, 325, 354, 375, 320.1, 360; 514/2, 44; 530/350, 387.1, 388.22, 388.1, 388.23; 536/23.1, 24.3, 24.31, 24.33, 24.5

(56) References Cited

U.S. PATENT DOCUMENTS

| | | | |
|---|---|---|---|
| 4,806,523 | 2/1989 | Bentz et al. | 514/2 |
| 4,971,952 | 11/1990 | Bentz et al. | 514/12 |
| 5,147,854 | 9/1992 | Newman | 514/12 |
| 5,300,292 | 4/1994 | Ulich | 424/85.2 |
| 5,376,368 | 12/1994 | Ulich | 424/85.2 |
| 5,387,576 | 2/1995 | Mitrani | 514/2 |
| 5,583,103 | 12/1996 | Ruoslahti et al. | 514/8 |
| 5,595,722 | 1/1997 | Grainger et al. | 424/9.2 |
| 5,674,483 | * 10/1997 | Tu et al. | 424/85.2 |

OTHER PUBLICATIONS

Zhang et al., American Journal of Pathology, vol. 147, No. 2, Aug. 1995, pp. 352–361.*
Zhang et al., Journal of Immunology, Jan. 15, 1997, 158: 954–959, Aug. 1995.*
Giri, S.N. et al. Thorax 48 (10), 959–966 (1993).*
Wahl, S.M. et al. J. Exp Med. 177 (1), 225–230 (Jan. 1, 1993).*
Khalil, N. et al. Am. J. Physiol. 267 (5 Pt 1), L498–L507 (Nov. 1994).*
Jachimczak, P. et al. Int. J. Cancer 65, 332–337 (Jan 26, 1996).*
Branch, A.D. Tibs, vol. 23, Feb. 1998, pp. 45–50.*
Stein, CA. Nature Biotechnology, vol. 17, Aug. 1999, pp. 751–752.*
Flanagan, W.M. et al. Nature Biotechnology, vol. 17, Jan. 1999, 48–52.*
Crooke, S.T. Chapter 1, in Antisense Reasearch and Application, (ed. Stanley Crooke), springer–Verlag, New York, 1998, pp. 1–50.*
Anderson, W.F. et al. Nature, vol. 392, Supp, Apr. 30, 1998, pp. 25–30.*
Gura, T. Science, vol. 278, Nov. 7, 1997, pp. 1041–1042.*
Wess, G. DDT, vol. 1, No. 12, Dec. 1996, pp. 529–532.*
Lloyd, A.W. DDT, vol. 2, No. 10, Oct. 1997, pp. 397–398.*
Goldman, M.E. DDT, vol. 2, No. 9, Sep. 1997, pp. 357–358.*
Black et al., *Am. J. Physiol.*, 271:L910–L917 (1996).
Broekelmann et al., *Proc. Natl. Acad. Sci. USA*, 88:6642–6 (1991).
Deguchi, *Ann. Rheum. Dis.*, 51:362–365 (1992).
Denis, *Immunology*, 82:584–590 (1994).
Khalil et al., *Am. J. Respir. Cell Mol. Biol.*, 14:131–138 (1996).
Ohno et al., *Am. J. Respir. Cell Mol. Biol.*, 15:404–409 (1996).
Romberger et al., *Am. J. Respir. Cell Mol. Biol.*, 7:149–155 (1992).
Uhl et al., *Am. J. Respir. Crit. Care Med.*, 154:1834–1842 (1996).
Vignola et al., *Clin. Exp. Immunol.*, 106:114–119 (1996).
Atsuta et al., *Int. Arch. Allergy Immunol.*, 108:31–35 (1995).
Aubert et al., *Thorax*, 49:225–232 (1994).
Gauldie et al., *Ann. N.Y. Acad. Sci.*, 796:235–244 (1996).
Lawrence, *Eur. Cytokine Netw.*, 7:363–374 (1996).
Martinet et al., *Arch. Toxicol. Suppl.*, 18:127–139 (1996).
Wangoo et al., *J. Clin. Pathol.*, 48:339–345 (1995).

* cited by examiner

Primary Examiner—Remy Yucel
Assistant Examiner—Mark L. Shibuya
(74) Attorney, Agent, or Firm—Sheridan Ross P.C.

(57) ABSTRACT

The present invention relates to a method to protect a mammal from a disease involving inflammation by treating that mammal with a TGFβ-regulating agent. The present invention also relates to a method for prescribing treatment for a respiratory disease involving an inflammatory response and a method for monitoring the success of a treatment for a respiratory disease involving an inflammatory response in a mammal. Also included in the present invention is a formulation comprising a TGFβ-regulating agent and a compound capable of enhancing the effectiveness of the TGFβ-regulating agent at protecting a mammal from a disease involving inflammation.

38 Claims, 11 Drawing Sheets

METHOD FOR TREATMENT OF INFLAMMATORY DISEASE

CROSS-REFERENCE TO RELATED APPLICATION

This application claims benefit of U.S. Provisional Application No. 60/063,605, filed Jun. 10, 1997, and entitled, "METHOD FOR TREATMENT OF INFLAMMATORY DISEASE", which is incorporated herein by reference in its entirety.

FIELD OF THE INVENTION

The present invention relates to a method to protect a mammal from a disease involving inflammation, in particular, a respiratory disease involving inflammation.

BACKGROUND OF THE INVENTION

Diseases involving inflammation are characterized by the influx of certain cell types and mediators, the presence of which can lead to tissue damage and sometimes death. Diseases involving inflammation are particularly harmful when they afflict the respiratory system, resulting in obstructed breathing, hypoxemia, hypercapnia and lung tissue damage. Obstructive diseases of the airways are characterized by airflow limitation (i.e., airflow obstruction or narrowing) due to constriction of airway smooth muscle, edema and hypersecretion of mucous leading to increased work in breathing, dyspnea, hypoxemia and hypercapnia. While the mechanical properties of the lungs during obstructed breathing are shared between different types of obstructive airway disease, the pathophysiology can differ.

A variety of inflammatory agents can provoke airflow limitation including allergens, cold air, exercise, infections and air pollution. In particular, allergens and other agents in allergic or sensitized mammals (i.e., antigens and haptens) cause the release of inflammatory mediators that recruit cells involved in inflammation. Such cells include lymphocytes, eosinophils, mast cells, basophils, neutrophils, macrophages, monocytes, fibroblasts and platelets. Inflammation results in airway hyperresponsiveness. A variety of studies have linked the degree, severity and timing of the inflammatory process with the degree of airway hyperresponsiveness. Thus, a common consequence of inflammation is airflow limitation and/or airway hyperresponsiveness.

Asthma is a significant disease of the lung which effects nearly 12 million Americans. Asthma is typically characterized by periodic airflow limitation and/or hyperresponsiveness to various stimuli which results in excessive airways narrowing. Other characteristics can include inflammation of airways, eosinophilia and airway fibrosis.

Airway fibrosis due to the deposition of collagen or provisional matrix beneath the basement membrane is a consistent finding in asthma patients, even in the airways of patients with mild asthma. This deposition of collagen is not altered by steroid treatment. Clinical studies have shown a positive correlation between airway fibrosis and airway dysfunction (e.g., airflow limitation or airways hyperresponsiveness). The inflammatory mechanisms which result in this collagen deposition are unknown and more importantly, the functional significance of airway fibrosis is not understood. There is a need to determine the mechanisms which link inflammation, airways remodeling and pathophysiology in asthma since such mechanisms are likely to have a bearing on disease severity and the efficaciousness of therapeutics, as well as their role in other inflammatory diseases.

Asthma prevalence (i.e., both incidence and duration) is increasing. The current prevalence approaches 10% of the population and has increased 25% in the last 20 years. Of more concern, however, is the rise in the death rate. When coupled with increases in emergency room visits and hospitalizations, recent data suggests that asthma severity is rising. While most cases of asthma are easily controlled, for those with more severe disease, the costs, the side effects and all too often, the ineffectiveness of the treatment, present serious problems. Fibroproliferative responses to chronic antigen exposure may explain both asthma severity and poor responses to therapy, especially if treatment is delayed. The majority of patients with asthma have very mild symptoms which are easily treated, but a significant number of asthmatics have more severe symptoms. Moreover, chronic asthma is associated with the development of progressive and irreversible airflow limitation due to some unknown mechanism.

Currently, therapy for treatment of inflammatory diseases such as moderate to severe asthma predominantly involves the use of glucocorticosteroids. Other anti-inflammatory agents that are used to treat inflammatory diseases include cromolyn and nedocromil. Symptomatic treatment with beta-agonists, anticholinergic agents and methyl xanthines are clinically beneficial for the relief of discomfort but fail to stop the underlying inflammatory processes that cause the disease. The frequently used systemic glucocorticosteroids have numerous side effects, including, but not limited to, weight gain, diabetes, hypertension, osteoporosis, cataracts, atherosclerosis, increased susceptibility to infection, increased lipids and cholesterol, and easy bruising. Aerosolized glucocorticosteroids have fewer side effects but can be less potent and have significant side effects, such as thrush.

Other anti-inflammatory agents, such as cromolyn and nedocromil are much less potent and have fewer side effects than glucocorticosteroids. Anti-inflammatory agents that are primarily used as immunosuppressive agents and anti-cancer agents (i.e., cytoxan, methotrexate and Immuran) have also been used to treat inflammation with mixed results. These agents, however, have serious side effect potential, including, but not limited to, increased susceptibility to infection, liver toxicity, drug-induced lung disease, and bone marrow suppression. Thus, such drugs have found limited clinical use for the treatment of most airway hyperresponsiveness lung diseases.

The use of anti-inflammatory and symptomatic relief reagents is a serious problem because of their side effects or their failure to attack the underlying cause of an inflammatory response. There is a continuing requirement for less harmful and more effective reagents for treating inflammation. Thus, there remains a need for processes using reagents with lower side effect profiles and less toxicity than current anti-inflammatory therapies.

SUMMARY OF THE INVENTION

The present invention provides for a method and a formulation for protecting a mammal from diseases involving inflammation. The present invention is particularly advantageous in that it targets a specific family of molecules which are shown herein to play a complex and prominent role in both inflammation and airway fibrosis, thereby reducing the side effects and toxicity profiles frequently associated with non-specific anti-inflammatory therapies.

One embodiment of the present invention includes a method to protect a mammal from a respiratory disease involving an inflammatory response, the method comprising administering to the mammal a TGFβ-regulating agent selected from the group of a pan-specific TGFβ-inhibiting agent, a TGFβ1-stimulating agent, TGFβ1, a TGFβ2-inhibiting agent, a TGFβ3-inhibiting agent and combinations thereof. The method of the present invention is particularly effective in protecting mammals from respiratory diseases by reducing airway hyperresponsiveness, decreasing methacholine responsiveness, decreasing lung inflammation and/or decreasing airways fibroproliferation. Preferably, the method of the present invention reduces the airflow limitation of a mammal such that the $FEV_1/FVC$ value of the mammal is improved by at least about 5% (or at least 100 cc or PGFRg 10 L/min). Administration of the TGFβ-regulating agent can result in an improvement in a mammal's $PC_{20methacholine}FEV_1$ value such that the $PC_{20methacholine}FEV_1$ value obtained before administration of the TGFβ-regulating agent when the mammal is provoked with a first concentration of methacholine is the same as the $PC_{20methacholine}FEV_1$ value obtained after administration of the TGFβ-regulating agent when the mammal is provoked with double the amount of the first concentration of methacholine.

Diseases from which a mammal can be protected by the method of the present invention include, but are not limited to, chronic obstructive pulmonary diseases of the airways, as well as diseases including asthma, allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumotitis, occupational asthma, sarcoid, reactive airway disease syndrome, interstitial lung disease, hypereosinophilic syndrome, rhinitis, sinusitis, and parasitic lung disease. The method of the present invention is particularly useful for protecting a mammal from asthma, occupational asthma or reactive airway disease syndrome.

In preferred embodiments, a TGFβ-regulating agent useful in the method of the present invention includes an antibody, an antisense oligonucleotide, a TGFβ receptor antagonist, a TGFβ receptor agonist, a TGFβ-specific ribozyme, an isolated TGFβ1 protein, and/or an isolated nucleic acid molecule encoding a TGFβ1 protein, which in some embodiments, is operatively linked to a transcription control sequence. Preferred antibodies useful in the method of the present invention include a pan-specific TGFβ antibody, a TGFβ2-specific antibody, a TGFβ3-specific antibody, a pan-specific TGFβ receptor-specific antibody, a TGFβ1 receptor-specific antibody, a TGFβ2 receptor-specific antibody and a TGFβ3 receptor-specific antibody. Preferred antisense oligonucleotides useful in the method of the present invention include antisense oligonucleotides that hybridize under stringent hybridization conditions to a nucleic acid molecule encoding a protein selected from the group of a TGFβ2 protein and a TGFβ3 protein.

When the TGFβ-regulating agent of the present invention is an isolated nucleic acid molecule encoding a TGFβ1 protein, in one embodiment, the nucleic acid molecule is administered to the mammal complexed with a liposome delivery vehicle or a in a viral vector delivery vehicle. A preferred viral vector delivery vehicle is an adenovirus vector. A nucleic acid molecule encoding a isolated nucleic acid molecule encoding a TGFβ1 protein, when administered to the mammal, is typically expressed in the cells of the mammal.

A TGFβ-regulating agent is preferably administered to the mammal by a route which includes, but is not limited to, oral, nasal, topical, inhaled, transdermal, rectal or parenteral routes, with intramuscular, subcutaneous, inhaled and nasal routes being more preferred. In one embodiment, the TGFβ-regulating agent is administered in an amount between about 0.1 microgram×kilogram$^{-1}$ and about 10 milligram× kilogram$^{-1}$ body weight of a mammal. In another embodiment, a TGFβ-regulating agent is administered in a pharmaceutically acceptable excipient. A preferred mammal to which to administer a TGFβ-regulating agent is a human.

Another embodiment of the present invention relates to a method for protecting a mammal from airways fibrosis associated with a respiratory disease involving inflammation. Such method comprises administering to a mammal a TGFβ-regulating agent selected form the group of a pan-specific TGFβ-inhibiting agent, a TGFβ1-stimulating agent, TGFβ1, a TGFβ2-inhibiting agent, a TGFβ3-inhibiting agent and combinations thereof. Other embodiments of such a method are as described above.

Another embodiment of the present invention is directed to a method for prescribing treatment for a respiratory disease involving an inflammatory response, comprising: (1) administering to a mammal a TGFβ-regulating agent selected from the group of a pan-specific TGFβ-inhibiting agent, a TGFβ1-stimulating agent, TGFβ1, a TGFβ2-inhibiting agent, a TGFβ3-inhibiting agent and combinations thereof; (2) measuring a change in lung function in response to a provoking agent in the mammal to determine if the TGFβ-regulating agent is capable of modulating airway hyperresponsiveness; and (3) prescribing a pharmacological therapy effective to reduce inflammation based upon the changes in lung function. Preferred provoking agents include direct and indirect stimuli. Particularly preferred provoking agents include, an allergen, methacholine, a histamine, a leukotriene, saline, hyperventilation, exercise, sulfur dioxide, adenosine, propranolol, cold air, an antigen, bradykinin, acetylcholine, a prostaglandin, ozone, environmental air pollutants or mixtures thereof. The step of measuring can include measuring a value selected from the group of $FEV_1$, $FEV_1/FVC$, $PC_{20methacholine}FEV_1$, post-enhanced pause (Penh), conductance, dynamic compliance, lung resistance ($R_L$), airway pressure time index (APTI), and peak flow.

Another embodiment of the present invention includes a method for long-term care of a patient having a disease involving inflammation, the method comprising: (1) assessing the status of the disease of a patient; (2) administering to the patient a TGFβ-regulating agent; and (3) providing long-term care of the patient by preventing significant exposure of the patient to the cause of the disease. Preferably, the status of the disease is assessed by determining a characteristic of the disease, such as determining the form, severity and complications of the disease. In addition, the status of the disease is assessed by determining, for example, a causative agent and/or a provoking agent of the disease. From the assessment of the causative and/or provoking agent of the disease, long-term care can be provided by minimizing the exposure of the patient to the causative and/or provoking agent of the disease.

The present invention also includes a formulation for protecting a mammal from a disease involving inflammation, comprising a TGFβ-regulating agent. Such a formulation can also include an anti-inflammatory agent which enhances the ability of the TGFβ-regulating agent to protect a mammal from a disease involving inflammation, and in some embodiments, includes a pharmaceutically acceptable excipient. Suitable TGFβ-regulating agents have been described above. Preferred pharmaceutically acceptable excipients include biocompatible polymers, other polymeric matrices, capsules, microcapsules, microparticles, bolus preparations, osmotic pumps, diffusion devices, liposomes, lipospheres, viral vectors, ribozymes and transdermal delivery systems. Preferred anti-inflammatory agents include, but are not limited to, an antigen, an allergen, a hapten, proinflammatory cytokine antagonists, proinflammatory cytokine receptor antagonists, anti-CD23, anti-IgE, anticholinergics, immunomodulating drugs, leukotriene synthesis inhibitors, leukotriene receptor antagonists, glucocorticosteroids, steroid chemical derivatives, anti-cyclooxygenase agents, anti-cholinergic agents, beta-adrenergic agonists, methylxanthines, anti-histamines, cromones, zyleuton, anti-CD4 reagents, anti-IL-5 reagents, surfactants, anti-thromboxane reagents, anti-serotonin reagents, ketotiphen, cytoxin, cyclosporin, methotrexate, macrolide antibiotics, heparin, low molecular weight heparin, and mixtures thereof.

BRIEF DESCRIPTION OF THE DRAWINGS OF THE INVENTION

DETAILED DESCRIPTION OF THE INVENTION

Figure 1:
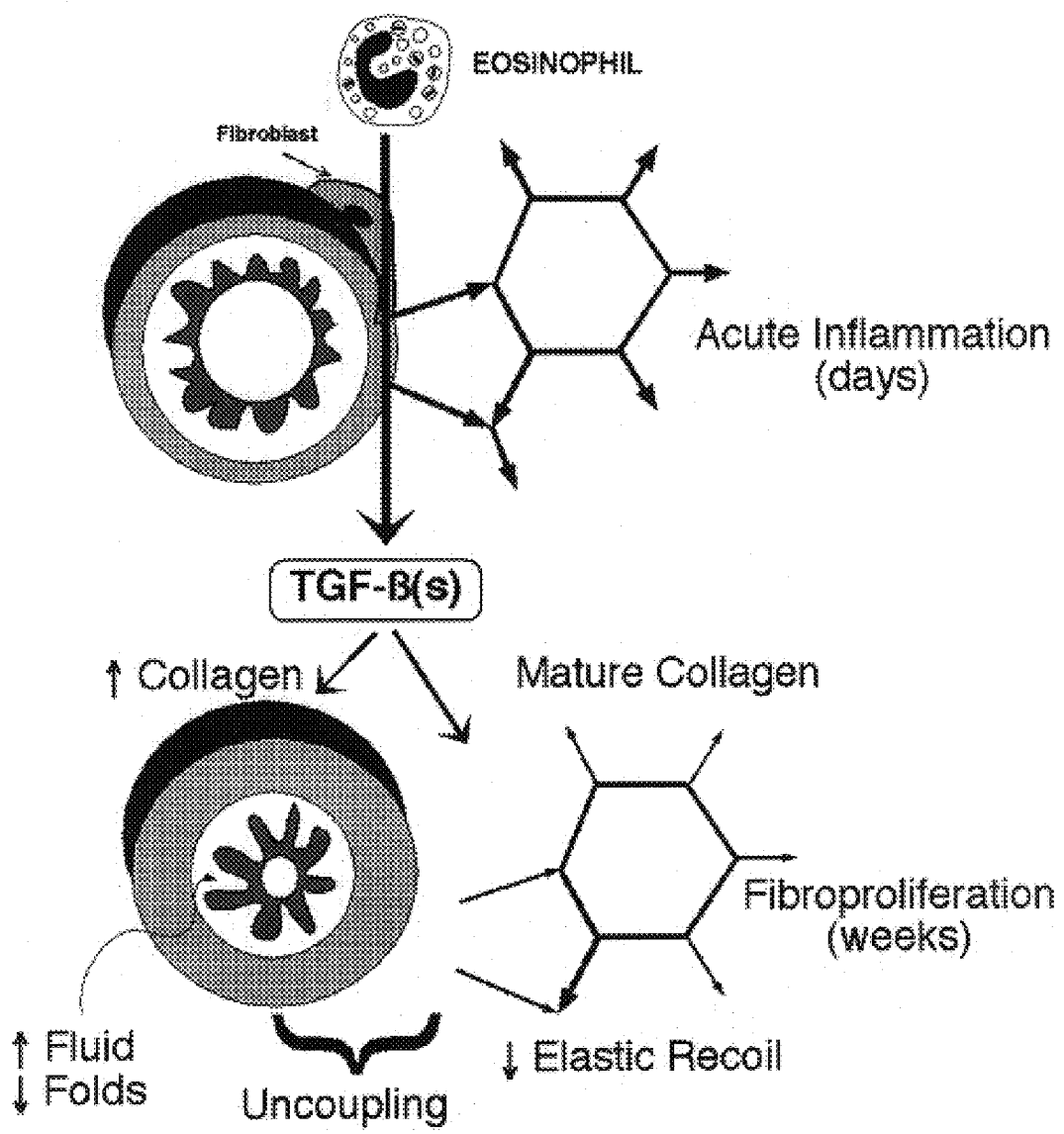
FIG. 1 is a schematic representation of the mechanisms and processes by which an eosinophilic inflammation leads to an inflammatory-dependent and then fibroproliferative-dependent change in airways hyperresponsiveness.

The present invention generally relates to a method and formulation to protect a mammal from a disease involving inflammation. The present inventors demonstrate for the first time herein a direct mechanistic link between the isoforms of the cytokine, TGFβ, and collagen deposition and airways dysfunction. Unexpectedly, the present inventors have discovered that the differential regulation of TGFβ isoforms results in either significant inhibition or significant enhancement of inflammation. Provided herein for the first time is evidence that the three known TGFβ isoforms play distinct and opposing roles in inflammatory disease. At the time of the present invention, the specific role of the TGFβ in inflammatory disease, and particularly asthma, was not well understood, and remains in fact, controversial. Moreover, the three isoforms of TGFβ are generally thought to exhibit similar biologic effects, and as such, have been typically studied nondiscriminantly, and are rarely referenced individually.

TGFβ (i.e., the group of TGFβs) has complex biological activities which can be immunoregulatory (both suppressive and stimulating) as well as both proliferative and antiproliferative. Although it is thought that TGFβ suppresses proliferation of most cells and induces T cell responses which do not damage tissues, TGFβ is also known to stimulate the growth of some mesenchymal cells and enhance the formation of cellular matrix.

At the time of the present invention, antigen presentation and T-cell based immunity are believed to play a central role in the pathogenesis of inflammatory respiratory diseases such as asthma. Recent studies in murine models show support for and against a role for the eosinophil (a producer of TGFβ) in mediating airways hyperresponsiveness, however, its role in airways structural changes is largely unexplored. Prior to the present invention, support for a role for TGFβ in inflammatory diseases such as asthma has been both controversial and circumstantial. For example, it has been shown that elevated levels of TGFβ (but not EGF or GM-CSF) in the airway is correlated with the thickness of the basement membrane. It has also been found that TGFβ colocalizes to eosinophils in biopsy specimens from asthmatic patients, and that polymorphisms exist in the TGFβ promoter of severe asthmatics. In addition, eosinophil MBP synergizes with TGFβ, in part due to its charge, to increase cytokine production by fibroblasts, and TGFβ demonstrates a sudden and transient peak prior to the maximal collagen synthesis. Prior to the present invention, many investigators have suggested that all of the TGFβ isoforms play a central role in the induction of fibrogenesis and increased inflammation in airways. In other inflammatory processes, many investigators have suggested that all of the TGFβ isoforms play an inhibitory role in such processes.

In contrast to the above teachings regarding the role of TGFβ, and particularly TGFβ1, in respiratory inflammatory diseases, the present inventors provide evidence herein that TGFβ does not increase fibrosis and airways hyperresponsiveness in vivo and may actually enhance resistance to airways hyperresponsiveness, whereas TGFβ2 and/or TGFβ3 increase lung inflammation and development of airways fibrosis and airways hyperresponsiveness. This unexpected finding suggests heretofore unappreciated methods for treating inflammatory diseases. The present invention provides in vivo evidence which directly links the fibroproliferative processes in the airway walls to airways dysfunction, demonstrates the distinct and opposing roles of TGFβ isoforms in airway remodeling, and determines the pathophysiologic mechanisms which link airway fibrosis to increased airways resistance and responsiveness.

Without being bound by theory, the present inventor believes that this heretofore undemonstrated combination of pathophysiologic sequelae results in excessive airways narrowing by the mechanism illustrated in FIG. 1. FIG. 1 is a schematic representation of the mechanisms and processes by which an eosinophilic inflammation leads to an inflammatory-dependent and then fibroproliferative-dependent change in airways hyperresponsiveness in which TGFβ2 and/or TGFβ3, but not TGFβ1, play a direct, proinflammatory role. Collagen deposition or other aspects of airway remodeling are postulated to lead to both chronic airflow limitation and a loss of parenchymal recoil which uncouples the alveolar attachments, and a loss of airway/parenchymal interdependence which results in uninhibited airways narrowing.

One embodiment of the present invention relates to a method to protect a mammal from a disease involving inflammation, comprising administering to the mammal a transforming growth factor β (TGFβ)-regulating agent. Such a TGFβ-regulating agent, includes, but is not limited to a pan-specific TGFβ-inhibiting agent, a TGFβ1-stimulating agent, TGFβ1, a TGFβ2-inhibiting agent, a TGFβ3-inhibiting agent and combinations thereof. In one embodiment, a TGFβ-regulating agent preferably includes a TGFβ2-inhibiting agent and/or a TGFβ3-inhibiting agent. In this embodiment, TGFβ1 is not regulated. In a further embodiment, a TGFβ-regulating agent preferably includes a TGFβ2-inhibiting agent and/or a TGFβ3-regulating agent, which can be administered in combination with a TGFβ1-stimulating agent. A TGFβ-regulating agent also includes TGFβ1, which can be administered in the form of an isolated TGFβ1 protein and/or an isolated nucleic acid molecule encoding a TGFβ1 protein. In yet another embodiment, a TGFβ-regulating agent is a pan-specific TGFβ-inhibiting agent.

At the time of the present invention, there are at least 3 isoforms of TGFβ thought to be important in mammals, which are referred to herein as TGFβ1, TGFβ2 and TGFβ3. Human TGFβ is translated from a 2.5 kb mRNA as a 391 amino acid propeptide. Murine and human TGFβ differ by only one amino acid residue. As such, the molecule appears to be highly conserved and its action is therefore not species-specific. Therefore, mammalian TGFβ-regulatory agents useful in the present invention are useful for regulating TGFβ, TGFβ subunits, protein chains or fragments of TGFβ, from any species of mammal. Functionally mature TGFβ1 is obtained by enzymatic cleavage of 112 amino acids at the carboxy-terminus of the propeptide. It is composed of two identical 12.5 kD subunits that are held together by a number of interchain disulfide bonds. TGFβ2, also a homodimer, is about 63% homologous to TGFβ1. TGFβ3 is a heterodimer formed from one chain of TGFβ1 and one chain of TGFβ2. TGFβ binds to a high-affinity cell surface receptor. There are about 80,000 TGFβ receptors (TGFβ R) on fibroblasts, and about 250 TGFβ receptors on lymphocytes.

TGFβ is a potent stimulus for collagen and fibronectin synthesis by the fibroblast and is abundantly present in the airways and lung. TGFβ is unique among the cytokines, because when it is secreted, it is bound noncovalently to a latency-associated peptide which is biologically inactive. TGFβ activation occurs via extremes in pH, heat, or thrombospondin-1, or to activation or release from the extracellular matrix due to proteinases of the serine protease family (e.g., plasmin, mast cell chymase and leukocyte elastase). In addition, IFNγ has been reported to inhibit TGFβ activation and decrease procollagen formation. Post secretory activation may therefore be a more important control point for TGFβ than transcription or translation.

According to the present invention, "TGFβ" refers to known TGFβ proteins, including one or more of all isoforms of TGFβ (i.e., TGFβ1, TGFβ2 or TGFβ3), although use of the term TGFβ is not necessarily limited to all three isoforms as a group. Generally, when referring to a specific characteristic or function of a particular TGFβ isoform, such TGFβ isoform will be specifically referred to herein by the isoform name. As used herein, a "TGFβ protein" or a "TGFβ molecule" can refer to any portion of a TGFβ protein or molecule including the full length protein, a subunit (e.g., the α or β chain), a portion of a full length protein or molecule, or a portion of a subunit (i.e., a fragment). TGFβ can also refer to proteins encoded by naturally occurring allelic variants that have a similar, but not identical, nucleic acid sequence to wild-type TGFβ-encoding nucleic acid sequences. A naturally occurring allelic variant is a gene that occurs at essentially the same locus (or loci) in the genome as the TGFβ gene, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions).

According to the present invention, a TGFβ-regulating agent can be any agent which regulates the production, concentration (i.e., level or amount in a mammal systemically and/or in a given microenvironment) and/or function of any one or more of the TGFβ isoforms. Preferably, a TGFβ-regulating agent is selected from the group of a pan-specific TGFβ-inhibiting agent, a TGFβ1-stimulating agent, TGFβ1, a TGFβ2-inhibiting agent and a TGFβ3-inhibiting agent. According to the present invention, a "pan-specific" agent refers to an agent which has activity on all TGFβ isoforms (i.e., is not selective for any one isoform). For example, a pan-specific anti-TGFβ antibody is capable of binding to any of the TGFβ isoforms. As used herein, the term "regulate" or "regulating" can be used interchangeably with the term "modulate". To "regulate" TGFβ in the present invention refers to specifically controlling, or influencing the production or function (i.e., activity) of TGFβ, and can include regulation by activation, stimulation, inhibition, alteration or modification of TGFβ and/or TGFβ-producing cells (including both endogenous and recombinant TGFβ-producing cells), and of molecules which interact with TGFβ or are directly activated by TGFβ, such as TGFβ receptors and molecules within the TGFβ receptor signal transduction pathway. As used herein, the phrase "TGFβ receptor" includes molecules and complexes of molecules which bind to TGFβ and are capable of receiving a signal (i.e., via binding of TGFβ) and transmitting such a signal across the plasma membrane of a cell.

Regulation of TGFβ can be accomplished by a mode of regulation including regulation of the production of TGFβ (e.g., gene or protein expression, both endogenously and recombinantly); by regulation of the physical location of the TGFβ molecule, such as by regulating the translocation of the molecule to the membrane; or by regulating the activity of TGFβ (e.g., regulating the activation or the function of TGFβ, such as by preventing activation of TGFβ, deactivating TGFβ that is activated, or preventing the interaction of TGFβ with its receptor).

Techniques or methods by which one or more of the above modes of regulation of TGFβ can be accomplished include, but are not limited to, (a) degrading TGFβ, (b) binding a regulatory compound to TGFβ, (c) regulating transcription of TGFβ, (d) regulating translation of TGFβ, and (e) regulating the interaction of TGFβ with another molecule such as its receptor (e.g., by physically blocking the interaction between two molecules or by moving one molecule relative to the other such that interaction between the two can not occur).

As discussed above, a TGFβ-regulating agent of the present invention can be any agent (e.g., compound, drug, nucleic acid molecule, protein) which regulates the production and/or function of one or more TGFβ isoforms, including agents which regulate all TGFβ isoforms. TGFβ-regulating agents can regulate TGFβ directly, or can be agents that regulate cells that produce TGFβ such that TGFβ production is enhanced, reduced or blocked. Examples of cells which produce TGFβ, and on which a TGFβ-regulating agent can act, are eosinophils, T cells and macrophages. In a preferred embodiment, production of TGFβ by eosinophils is regulated. Additionally, a TGFβ-regulating agent of the present invention can include TGFβ itself, in the form of either an isolated protein (i.e., an exogenous protein) or an isolated (i.e., recombinant) nucleic acid molecule encoding a TGFβ protein. Preferably, such an isolated protein is TGFβ1.

TGFβ-regulating agents as referred to herein include, for example, compounds that are products of rational drug design, natural products, and compounds having partially defined TGFβ regulatory properties. A TGFβ-regulatory agent can be a protein-based compound, a carbohydrate-based compound, a lipid-based compound, a nucleic acid-based compound, a natural organic compound, a synthetically derived organic compound, an antibody, or fragments thereof. Particularly preferred TGFβ-regulatory agents of the present invention include drugs which regulate the production and/or function of TGFβ(any isoform or pan-specific); antibodies which selectively bind to TGFβ2 and/or TGFβ3; pan-specific TGFβ antibodies; antibodies which selectively bind to TGFβ2 and/or TGFβ3 receptors such that the activity of these receptors is blocked; antibodies which selectively bind to TGFβ1 receptors such that the activity of this receptor is stimulated; soluble TGFβ2 and/or TGF3 receptors; TGFβ1 receptor agonists which bind to TGFβ1 receptors and enhance receptor activity as compared to receptor binding by endogenous TGFβ1; TGFβ2 and/or TGFβ3 receptor antagonists which bind to TGFβ2 or TGFβ3 receptors and inhibit receptor activity; antisense oligonucleotides that hybridize under stringent hybridization conditions with TGFβ2 and/or TGFβ3; TGFβ-specific ribozymes that specifically target and inhibit RNA encoding TGFβ2 and/or TGFβ3, isolated TGFβ1 proteins and homologues thereof; and/or isolated nucleic acid molecules encoding TGFβ1 proteins or homologues thereof, and naturally occurring allelic variants of such nucleic acid molecules.

A TGFβ-regulatory agent can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the same building blocks) or by rational drug design. See for example, Maulik et al., 1997, Molecular Biotechnology: Therapeutic Applications and Strategies, Wiley-Liss, Inc., which is incorporated herein by reference in its entirety.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands against a desired target, and then optimize the lead molecules by either random or directed design strategies. Methods of molecular diversity are described in detail in Maulik, et al., ibid.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as potential TGFβ-regulatory agents by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi).

A TGFβ-regulating agent which is an antibody is an antibody which selectively binds to a TGFβ protein or mimetope thereof. Such an antibody can be referred to herein as an anti-TGFβ antibody. Anti-TGFβ antibodies can selectively bind to any one or more of the TGFβ isoforms. As used herein, the term "selectively binds to" refers to the ability of such an antibody to preferentially bind to TGFβ (including any isoforms, fragments, subunits and/or homologues of TGFβ) and mimetopes thereof. Antibodies useful in the present invention can be either polyclonal or monoclonal antibodies. Such antibodies can include, but are not limited to, neutralizing antibodies, non-neutralizing antibodies, and complement fixing antibodies. Antibodies useful in the present invention include functional equivalents such as antibody fragments and genetically-engineered antibodies, including single chain antibodies, that are capable of selectively binding to at least one of the epitopes of the protein or mimetope used to obtain the antibodies. Antibodies useful in the present invention can include chimeric antibodies in which at least a portion of the heavy chain and/or light chain of an antibody is replaced with a corresponding portion from a different antibody. For example, a chimeric antibody of the present invention can include an antibody having an altered heavy chain constant region (e.g., altered isotype), an antibody having protein sequences derived from two or more different species of mammal, and an antibody having altered heavy and/or light chain variable regions (e.g., altered affinity or specificity). Preferred antibodies are raised in response to proteins, peptides or mimetopes thereof of TGFβ. More preferred antibodies are raised by proteins, or mimetopes thereof, that are encoded, at least in part, by a TGFβ nucleic acid molecule.

Anti-TGFβ antibodies (both monoclonal and polyclonal) useful in the present invention can, in one embodiment of the present invention, form immunocomplexes which inhibit the binding of TGFβ to a TGFβ receptor (TGFβR) and/or inhibit the internalization of TGFβ/TGFβR complexes into cells bearing such TGFβ receptors. An immunocomplex refers to a complex comprising an antibody and its ligand (i.e., antigen). According to the present invention, inhibition of binding refers to the ability of an anti-TGFβ antibody to preferably prevent the binding of TGFβ to at least about 50%, more preferably at least about 70%, and even more preferably at least about 90% of available TGFβ receptors. Inhibition of internalization of TGFβ/TGFβR complexes refers to the ability of an anti-TGFβ antibody to preferably prevent the internalization of TGFβ/TGFβR complexes on at least about 50%, more preferably at least about 70%, and even more preferably at least about 90% of the cells bearing TGFβ receptors in a mammal.

In one embodiment, a TGFβ-regulating agent can be an antisense oligonucleotide. As used herein, antisense oligonucleotides are short stretches of DNA or RNA that hybridize under stringent hybridization conditions to a specific complementary gene sequence (e.g., a portion of the gene sequence for TGFβ or its regulatory regions) or messenger RNA molecule and inhibit their action by physically blocking the template sequence. Strategies for development and evaluation of antisense oligonucleotides are known in the art and are described in Maulik et al., ibid. As used herein, stringent hybridization conditions refer to standard hybridization conditions under which nucleic acid molecules, including oligonucleotides, are used to identify molecules having similar nucleic acid sequences. Stringent hybridization conditions typically permit isolation of nucleic acid molecules having at least about 70% nucleic acid sequence identity with the nucleic acid molecule being used as a probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety. Such standard conditions are disclosed, for example, in Sambrook et al., ibid., which is incorporated by reference herein in its entirety (see specifically, pages 9.31–9.62, 11.7 and 11.45–11.61). Examples of such conditions include, but are not limited to, the following: Oligonucleotide probes of about 18–25 nucleotides in length with $T_m$'s ranging from about 50° C. to about 65° C., for example, can be hybridized to nucleic acid molecules typically immobilized on a filter (e.g., nitrocellulose filter) in a solution containing 5×SSPE, 1% Sarkosyl, 5×Denhardts and 0.1 mg/ml denatured salmon sperm DNA at 37° C. for about 2 to 12 hours. The filters are then washed 3 times in a wash solution containing 5×SSPE, 1% Sarkosyl at 37° C. for 15 minutes each. The filters can be further washed in a wash solution containing 2×SSPE, 1% Sarkosyl at 37° C. for 15 minutes per wash. Randomly primed DNA probes can be hybridized, for example, to nucleic acid molecules typically immobilized on a filter (e.g., nitrocellulose filter) in a solution containing 5×SSPE, 1% Sarkosyl, 0.5% Blotto (dried milk in water), and 0.1 mg/ml denatured salmon sperm DNA at 42° C. for about 2 to 12 hours. The filters are then washed 2 times in a wash solution containing 5×SSPE, 1% Sarkosyl at 42° C. for 15 minutes each, followed by 2 washes in a wash solution containing 2×SSPE, 1% Sarkosyl at 42° C. for 15 minutes each. For hybridizations between molecules larger than about 100 nucleotides, the $T_m$ (melting temperature) can be estimated by $T_m = 81.5° C. + 16.6(\log_{10}[Na^+]) + 0.41(\text{fraction } G+C) - 0.63(\%\text{formamide}) - (600/l)$, where l is the length of the hybrid in base pairs. Specific parameters that affect this equation are discussed in detail on page 9.51 of Sambrook et al., supra. For hybridizations between smaller nucleic acid molecules, $T_m$ can be calculated by: $T_m = 81.5 + 16.6(\log_{10}[Na^+]) + 0.41(\text{fraction } G+C) - (600/N)$, where N=the chain length (Sambrook et al., supra, page 11.46). Alternatively, $T_m$ can be calculated empirically as set forth in Sambrook et al., supra, pages 11.55 to 11.57.

In one embodiment, a TGFβ-regulating agent can be an isolated TGFβ1 protein. A TGFβ1 protein useful in the method of the present invention can, for example, be obtained from its natural source, be produced using recombinant DNA technology, or be synthesized chemically. As used herein, a TGFβ1 protein can be a full-length TGFβ 1 protein, a peptide of the protein, and particularly a peptide of such protein which retains the biological activity of the full length protein, or any homologue of such a protein, such as a TGFβ1 protein in which one or a few amino acids have been deleted (e.g., a truncated version of the protein, such as a peptide), inserted, inverted, substituted and/or derivatized (e.g., by glycosylation, phosphorylation, acetylation, myristoylation, prenylation, palmitation, amidation and/or addition of glycosylphosphatidyl inositol). A homologue of a TGFβ1 protein is a protein having an amino acid sequence that is sufficiently similar to a natural TGFβ1 protein amino acid sequence that a nucleic acid sequence encoding the homologue is capable of hybridizing under stringent conditions to (i.e., with) a nucleic acid molecule encoding the natural TGFβ1 protein (i.e., to the complement of the nucleic acid strand encoding the natural TGFβ1 protein amino acid sequence). A nucleic acid sequence complement of any nucleic acid sequence refers to the nucleic acid sequence of the nucleic acid strand that is complementary to (i.e., can form a complete double helix with) the strand for which the sequence is cited. TGFβ1 proteins useful in the method of the present invention include, but are not limited to, proteins encoded by nucleic acid molecules having full-length TGFβ1 protein coding regions; fusion proteins; chimeric proteins or chemically coupled proteins comprising combinations of different TGFβ1 proteins, or combinations of TGFβ proteins with other proteins, such as an antigen or allergen; and proteins encoded by nucleic acid molecules having partial TGFβ1 protein coding regions, wherein such proteins protect a mammal from a respiratory disease associated with inflammation, and particularly with airways fibroproliferation. According to the present invention, a TGFβ1 protein can also refer to proteins encoded by allelic variants, including naturally occurring allelic variants of nucleic acid molecules known to encode TGFβ1 proteins, that have similar, but not identical, nucleic acid sequences to naturally occurring, or wild-type, TGFβ1-encoding nucleic acid sequences. An allelic variant is a gene that occurs at essentially the same locus (or loci) in the genome as a TGFβ1 gene, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions).

In another embodiment, a TGFβ-regulating agent can be an isolated nucleic acid molecule encoding a TGFβ1 protein. According to the present invention, a nucleic acid molecule can include DNA, RNA, or derivatives of either DNA or RNA. A nucleic acid molecule of the present invention can include a ribozyme which specifically targets RNA encoding TGFβ. A nucleic acid molecule encoding a TGFβ1 protein can be obtained from its natural source, either as an entire (i.e., complete) gene or a portion thereof that is capable of encoding a TGFβ1 protein that protects a mammal from a respiratory disease associated with inflammation, and particularly with airways fibroproliferation, when such protein and/or nucleic acid molecule encoding such protein is administered to the mammal. In one embodiment of the present invention, a nucleic acid molecule encoding a TGFβ protein is an oligonucleotide that encodes a portion of a TGFβ protein. Such an oligonucleotide can include all or a portion of a regulatory sequence of a nucleic acid molecule encoding TGFβ. A nucleic acid molecule can also be produced using recombinant DNA technology (e.g., polymerase chain reaction (PCR) amplification, cloning) or chemical synthesis. Nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a TGFβ1 protein that is useful in the method of the present invention. An isolated, or biologically pure, nucleic acid molecule, is a nucleic acid molecule that has been removed from its natural milieu. As such, "isolated" and "biologically pure" do not necessarily reflect the extent to which the nucleic acid molecule has been purified.

A nucleic acid molecule homologue can be produced using a number of methods known to those skilled in the art (see, for example, Sambrook et al., *Molecular Cloning: A Laboratory Manual*, Cold Spring Harbor Labs Press, 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., TGFβ1 protein activity, as appropriate). Techniques to screen for TGFβ1 protein activity are known to those of skill in the art.

Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a TGFβ1 protein. In addition, the phrase "recombinant molecule" primarily refers to a nucleic acid molecule operatively linked to a transcription control sequence, but can be used interchangeably with the phrase "nucleic acid molecule" which is administered to a mammal.

As described above, a nucleic acid molecule encoding a TGFβ1 protein that is useful in a method of the present invention can be operatively linked to one or more transcription control sequences to form a recombinant molecule. The phrase "operatively linked" refers to linking a nucleic acid molecule to a transcription control sequence in a manner such that the molecule is able to be expressed when transfected (i.e., transformed, transduced or transfected) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in a recombinant cell useful for the expression of a TGFβ1 protein, and/or useful to administer to a mammal in the method of the present invention. A variety of such transcription control sequences are known to those skilled in the art. Preferred transcription control sequences include those which function in mammalian, bacterial, or insect cells, and preferably in mammalian cells. More preferred transcription control sequences include, but are not limited to, simian virus 40 (SV-40), β-actin, retroviral long terminal repeat (LTR), Rous sarcoma virus (RSV), cytomegalovirus (CMV), tac, lac, trp, trc, oxy-pro, omp/lpp, rrnB, bacteriophage lambda (λ) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, *Heliothis zea* insect virus, vaccinia virus and other poxviruses, herpesvirus, and adenovirus transcription control sequences, as well as other sequences capable of controlling gene expression in eukaryotic cells. Additional suitable transcription control sequences include tissue-specific promoters and enhancers (e.g., T cell-specific enhancers and promoters). Transcription control sequences of the present invention can also include naturally occurring transcription control sequences naturally associated with a gene encoding a TGFβ1 protein useful in a method of the present invention.

Recombinant molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention also contains secretory signals (i.e., signal segment nucleic acid sequences) to enable an expressed TGFβ1 protein to be secreted from a cell that produces the protein. Preferred signal segments include, but are not limited to, signal segments naturally associated with any of the heretofore mentioned TGFβ1 proteins.

One or more recombinant molecules of the present invention can be used to produce an encoded product (i.e., a TGFβ1 protein). In one embodiment, an encoded product is produced by expressing a nucleic acid molecule of the present invention under conditions effective to produce the protein. A preferred method to produce an encoded protein is by transfecting a host cell with one or more recombinant molecules having a nucleic acid sequence encoding a TGFβ1 protein to form a recombinant cell. Suitable host cells to transfect include any cell that can be transfected. Host cells can be either untransfected cells or cells that are already transformed with at least one nucleic acid molecule. Host cells of useful in the present invention can be any cell capable of producing a TGFβ1 protein, including bacterial, fungal, mammal, and insect cells. A preferred host cell includes a mammalian cell.

According to the present invention, a host cell can be transfected in vivo (i.e., by delivery of the nucleic acid molecule into a mammal), ex vivo (i.e., outside of a mammal for reintroduction into the mammal, such as by introducing a nucleic acid molecule into a cell which has been removed from a mammal in tissue culture, followed by reintroduction of the cell into the mammal); or in vitro (i.e., outside of a mammal, such as in tissue culture for production of a recombinant TGFβ1 protein). Transfection of a nucleic acid molecule into a host cell can be accomplished by any method by which a nucleic acid molecule can be inserted into the cell. Transfection techniques include, but are not limited to, transfection, electroporation, microinjection, lipofection, adsorption, and protoplast fusion. Preferred methods to transfect host cells in vivo include lipofection and adsorption.

A recombinant cell of the present invention comprises a host cell transfected with a nucleic acid molecule that encodes a TGFβ1 protein. It may be appreciated by one skilled in the art that use of recombinant DNA technologies can improve expression of transfected nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules encoding a TGFβ1 protein include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the host cell, and deletion of sequences that destabilize transcripts. The activity of an expressed recombinant TGFβ1 protein may be improved by fragmenting, modifying, or derivatizing nucleic acid molecules encoding such a protein.

According to the present invention, a TGFβ-regulating agent can be administered to any member of the vertebrate class, Mammalia, including, without limitation, primates, rodents, livestock and domestic pets. A preferred mammal to protect using a TGFβ-regulating agent includes a human, a cat, a dog and a horse.

As used herein, the phrase "to protect a mammal from a disease involving inflammation" refers to reducing the potential for an inflammatory response (i.e., a response involving inflammation) to an inflammatory agent (i.e., an agent capable of causing an inflammatory response, e.g., methacholine, histamine, an allergen, a leukotriene, saline, hyperventilation, exercise, sulfur dioxide, adenosine, propranolol, cold air, antigen and bradykinin). Preferably, the potential for an inflammatory response is reduced, optimally, to an extent that the mammal no longer suffers discomfort and/or altered function from exposure to the inflammatory agent. For example, protecting a mammal can refer to the ability of a compound, when administered to the mammal, to prevent a disease from occurring and/or cure or alleviate disease symptoms, signs or causes. In particular, protecting a mammal refers to modulating an inflammatory response to suppress (e.g., reduce, inhibit or block) an overactive or harmful inflammatory response. Also in particular, protecting a mammal refers to regulating cell-mediated immunity and/or humoral immunity (i.e., T cell activity and/or IgE activity). Protecting a mammal can also refer to a reduction or prevention of symptoms associated with the disease, such as a reduction or prevention of airways fibrosis. Disease refers to any deviation from normal health of a mammal and include disease symptoms as well as conditions in which a deviation (e.g., infection, gene mutation, genetic defect, etc.) has occurred but symptoms are not yet manifested.

In a preferred embodiment, the present invention protects a mammal from a disease which includes a lung disease caused by inflammation or a skin disease caused by inflammation (e.g., atopic dermatitis). In a more preferred embodiment, the present invention protects a mammal from a disease which includes a chronic obstructive pulmonary disease (COPD) of the airways (i.e., airway obstruction caused by infiltration of inflammatory cells, scarring, edema, smooth muscle hypertrophy/hyperplasia, smooth muscle contraction and narrowing due to secretions, e.g., mucous, by cells). In an even more preferred embodiment, the present invention protects a mammal from a disease which includes asthma, allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumotitis, occupational asthma (i.e., asthma, wheezing, chest tightness and cough caused by a sensitizing agent, such as an allergen, irritant or hapten, in the work place), sarcoid, reactive airway disease syndrome (i.e., a single exposure to an agent that leads to asthma), interstitial lung disease, hyper-eosinophilic syndrome, rhinitis, sinusitis, or parasitic lung disease. In a preferred embodiment, the present invention protects a mammal from asthma, occupational asthma and reactive airway disease syndrome.

In accordance with the present invention, acceptable protocols to administer a TGFβ-regulating agent include the mode of administration and the effective amount of a TGFβ-regulating agent administered to a mammal, including individual dose size, number of doses and frequency of dose administration. Determination of such protocols can be accomplished by those skilled in the art. Suitable modes of administration can include, but are not limited to, oral, nasal, topical, transdermal, rectal, and parenteral routes. Preferred parenteral routes can include, but are not limited to, subcutaneous, intradermal, intravenous, intramuscular and intraperitoneal routes. Preferred topical routes include inhalation by aerosol (i.e., spraying) or topical surface administration to the skin of a mammal.

According to the method of the present invention, an effective amount of a TGFβ-regulating agent to administer to a mammal comprises an amount that is capable of reducing airway hyperresponsiveness (AHR) and/or reducing airflow limitation and/or symptoms (e.g., shortness of breath, wheezing, dyspnea, exercise limitation or nocturnal awakenings), without being toxic to the mammal. More particularly, an effective amount of a TGFβ-regulating agent to administer to a mammal comprises an amount that is capable of reducing airways fibroproliferation (i.e., airways fibrosis), which includes reducing collagen deposition and progressive fibrotic remodeling of the airway wall. An amount that is toxic to a mammal comprises any amount that causes damage to the structure or function of a mammal (i.e., poisonous).

AHR refers to an abnormality of the airways that allows them to narrow too easily and/or too much in response to a stimulus capable of inducing airflow limitation. AHR can be a functional alteration of the respiratory system caused by inflammation or airway remodeling (e.g., such as by collagen deposition). Airflow limitation refers to narrowing of airways that can be irreversible or reversible. Airflow limitation or airway hyperresponsiveness can be caused by collagen deposition, bronchospasm, airway smooth muscle hypertrophy, airway smooth muscle contraction, mucous secretion, cellular deposits, epithelial destruction, alteration to epithelial permeability, alterations to smooth muscle function or sensitivity, abnormalities of the lung parenchyma and infiltrative diseases in and around the airways.

AHR can be measured by a stress test that comprises measuring a mammal's respiratory system function in response to a provoking agent (i.e., stimulus). AHR can be measured as a change in respiratory function from baseline plotted against the dose of a provoking agent (a procedure for such measurement and a mammal model useful therefore are described in detail below in the Examples). Respiratory function can be measured by, for example, spirometry, plethysmographically, peak flows, symptom scores, physical signs (i.e., respiratory rate), wheezing, exercise tolerance, use of rescue medication (i.e., bronchodialators) and blood gases. In humans, spirometry can be used to gauge the change in respiratory function in conjunction with a provoking agent, such as methacholine or histamine. In humans, spirometry is performed by asking a person to take a deep breath and blow, as long, as hard and as fast as possible into a gauge that measures airflow and volume. The volume of air expired in the first second is known as forced expiratory volume ($FEV_1$) and the total amount of air expired is known as the forced vital capacity (FVC). In humans, normal predicted $FEV_1$ and FVC are available and standardized according to weight, height, sex and race. An individual free of disease has an $FEV_1$ and a FVC of at least about 80% of normal predicted values for a particular person and a ratio of $FEV_1/FVC$ of at least about 80%. Values are determined before (i.e, representing a mammal's resting state) and after (i.e., representing a mammal's higher lung resistance state) inhalation of the provoking agent. The position of the resulting curve indicates the sensitivity of the airways to the provoking agent.

The effect of increasing doses or concentrations of the provoking agent on lung function is determined by measuring the forced expired volume in 1 second ($FEV_1$) and $FEV_1$ over forced vital capacity ($FEV_1/FVC$ ratio) of the mammal challenged with the provoking agent. In humans, the dose or concentration of a provoking agent (i.e., methacholine or histamine) that causes a 20% fall in $FEV_1$ ($PD_{20}FEV_1$) is indicative of the degree of AHR. $FEV_1$ and FVC values can be measured using methods known to those of skill in the art.

Pulmonary function measurements of airway resistance ($R_L$) and dynamic compliance ($C_L$) and hyperresponsiveness can be determined by measuring transpulmonary pressure as the pressure difference between the airway opening and the body plethysmograph. Volume is the calibrated pressure change in the body plethysmograph and flow is the digital differentiation of the volume signal. Resistance ($R_L$) and compliance ($C_L$) are obtained using methods known to those of skill in the art (e.g., such as by using a recursive least squares solution of the equation of motion). Airway resistance ($R_l$) and dynamic compliance ($C_l$) are described in detail in the Examples. It should be noted that measuring the airway resistance ($R_L$) value in a non-human mammal (e.g., a mouse) can be used to diagnose airflow obstruction similar to measuring the $FEV_1$ and/or $FEV_1/FVC$ ratio in a human.

A variety of provoking agents are useful for measuring AHR values. Suitable provoking agent include direct and indirect stimuli. Preferred provoking agents include, for example, an allergen, methacholine, a histamine, a leukotriene, saline, hyperventilation, exercise, sulfur dioxide, adenosine, propranolol, cold air, an antigen, bradykinin, acetylcholine, a prostaglandin, ozone, environmental air pollutants and mixtures thereof. Preferably, Mch is used as a provoking agent. Preferred concentrations of Mch to use in a concentration-response curve are between about 0.001 and about 100 milligram per milliliter (mg/ml). More preferred concentrations of Mch to use in a concentration-response curve are between about 0.01 and about 50 mg/ml. Even more preferred concentrations of Mch to use in a concentration-response curve are between about 0.02 and about 25 mg/ml. When Mch is used as a provoking agent, the degree of AHR is defined by the provocative concentration of Mch needed to cause a 20% drop of the $FEV_1$ of a mammal ($PC_{20methacholine}FEV_1$). For example, in humans and using standard protocols in the art, a normal person typically has a $PC_{20methacholine}FEV_1 > 8$ mg/ml of Mch. Thus, in humans, AHR is defined as $PC_{20methacholine}FEV_1 < 8$ mg/ml of Mch.

The effectiveness of a drug to protect a mammal from AHR in a mammal having or susceptible to AHR is measured in doubling amounts. For example, the effectiveness a mammal to be protected from AHR is significant if the mammal's $PC_{20methacholine}FEV_1$ is at 1 mg/ml before administration of the drug and is at 2 mg/ml of Mch after administration of the drug. Similarly, a drug is considered effective if the mammal's $PC_{20methacholine}FEV_1$ is at 2 mg/ml before administration of the drug and is at 4 mg/ml of Mch after administration of the drug.

In one embodiment of the present invention, an effective amount of a TGFβ-regulating agent to administer to a mammal includes an amount that is capable of decreasing methacholine responsiveness without being toxic to the mammal. A preferred effective amount of a TGFB-regulating agent comprises an amount that is capable of increasing the $PC_{20methacholine}FEV_1$ of a mammal treated with the a TGFB-regulating agent by about one doubling concentration towards the $PC_{20methacholine}FEV_1$ of a normal mammal. A normal mammal refers to a mammal known not to suffer from or be susceptible to abnormal AHR. A test mammal refers to a mammal suspected of suffering from or being susceptible to abnormal AHR.

In another embodiment, an effective amount of a TGFB-regulating agent according to the method of the present invention, comprises an amount that results in an improvement in a mammal's $PC_{20methacholine}FEV_1$ value such that the $PC_{20methacholine}FEV_1$ value obtained before administration of the a TGFB-regulating agent when the mammal is provoked with a first concentration of methacholine is the same as the $PC_{20methacholine}FEV_1$ value obtained after administration of the a TGFB-regulating agent when the mammal is provoked with double the amount of the first concentration of methacholine. A preferred amount of a TGFB-regulating agent comprises an amount that results in an improvement in a mammal's $PC_{20methacholine}FEV_1$ value such that the $PC_{20methacholine}FEV_1$ value obtained before administration of the a TGFB-regulating agent is between about 0.01 mg/ml to about 8 mg/ml of methacholine is the same as the $PC_{20methacholine}FEV_1$ value obtained after administration of the a TGFβ-regulating agent is between about 0.02 mg/ml to about 16 mg/ml of methacholine.

According to the present invention, respiratory function can be evaluated with a variety of static tests that comprise measuring a mammal's respiratory system function in the absence of a provoking agent. Examples of static tests include, for example, spirometry, plethysmographically, peak flows, symptom scores, physical signs (i.e., respiratory rate), wheezing, exercise tolerance, use of rescue medication (i.e., bronchodialators) and blood gases. Evaluating pulmonary function in static tests can be performed by measuring, for example, Total Lung Capacity (TLC), Thoracic Gas Volume (TgV), Functional Residual Capacity (FRC), Residual Volume (RV) and Specific Conductance (SGL) for lung volumes, Diffusing Capacity of the Lung for Carbon Monoxide (DLCO), arterial blood gases, including pH, $P_{O2}$ and $P_{CO2}$ for gas exchange. Both $FEV_1$ and $FEV_1/FVC$ can be used to measure airflow limitation. If spirometry is used in humans, the $FEV_1$ of an individual can be compared to the $FEV_1$ of predicted values. Predicted $FEV_1$ values are available for standard normograms based on the mammal's age, sex, weight, height and race. A normal mammal typically has an $FEV_1$ at least about 80% of the predicted $FEV_1$ for the mammal. Airflow limitation results in a $FEV_1$ or FVC of less than 80% of predicted values. An alternative method to measure airflow limitation is based on the ratio of $FEV_1$ and FVC ($FEV_1/FVC$). Disease free individuals are defined as having a $FEV_1/FVC$ ratio of at least about 80%. Airflow obstruction causes the ratio of $FEV_1/FVC$ to fall to less than 80% of predicted values. Thus, a mammal having airflow limitation is defined by an $FEV_1/FVC$ less than about 80%.

The effectiveness of a drug to protect a mammal having or susceptible to airflow limitation can be determined by measuring the percent improvement in $FEV_1$ and/or the $FEV_1/FVC$ ratio before and after administration of the drug. In one embodiment, an effective amount of a TGFβ-regulating agent comprises an amount that is capable of reducing the airflow limitation of a mammal such that the $FEV_1/FVC$ value of the mammal is at least about 80%. In another embodiment, an effective amount of a TGFβ- regulating agent comprises an amount that is capable of reducing the airflow limitation of a mammal such that the $FEV_1/FVC$ value of the mammal is improved by at least about 5%, or at least about 100 cc or PGFRG 10 L/min. In another embodiment, an effective amount of a TGFβ-regulating agent comprises an amount that improves a mammal's $FEV_1$ by at least about 5%, and more preferably by between about 6% and about 100%, more preferably by between about 7% and about 100%, and even more preferably by between about 8% and about 100% (or about 200 ml) of the mammal's predicted $FEV_1$.

It is within the scope of the present invention that a static test can be performed before or after administration of a provocative agent used in a stress test.

In another embodiment, an effective amount of a TGFβ-regulating agent for use with the method of the present invention, comprises an amount that is capable of reducing the airflow limitation of a mammal such that the variation of $FEV_1$ or PEF values of the mammal when measured in the evening before sleeping and in the morning upon waking is less than about 75%, preferably less than about 45%, more preferably less than about 15%, and even more preferably less than about 8%.

In yet another embodiment, an effective amount of a TGFβ-regulating agent for use with the method of the present invention, comprises an amount that reduces the level of IgE in the serum of a mammal to between about 0 to about 100 international units/ml, preferably between about 10 to about 50 international units/ml, more preferably between about 15 to about 25 international units/ml, and even more preferably about 20 international units/ml. The concentration of IgE in the serum of a mammal can be measured using methods known to those of skill in the art. In particular, the concentration of IgE in the serum of a mammal can be measured by, for example, using antibodies that specifically bind to IgE in an enzyme-linked immunoassay or a radioimmunoassay.

In another embodiment, an effective amount of a TGFβ-regulating agent for use with the method of the present invention, comprises an amount that reduces eosinophil blood counts in a mammal to preferably between about 0 and 470 cells/mm$^3$, more preferably to between about 0 and 300 cells/mm$^3$, and even more preferably to between about 0 and 100 cells/mm$^3$. Eosinophil blood counts of a mammal can be measured using methods known to those of skill in the art. In particular, the eosinophil blood counts of a mammal can be measured by vital stains, such as phloxin B or Diff Quick.

A suitable single dose of a TGFβ-regulating agent to administer to a mammal is a dose that is capable of protecting a mammal from an inflammatory response when administered one or more times over a suitable time period. In particular, a suitable single dose of a TGFβ-regulating agent comprises a dose that improves AHR by a doubling dose of a provoking agent or improves the static respiratory function of a mammal. A preferred single dose of a TGFβ-regulating agent comprises between about 0.1 microgram×kilogram$^{-1}$ and about 10 milligram×kilogram$^{-1}$ body weight of a mammal. A more preferred single dose of a TGFβ-regulating agent comprises between about 1 microgram×kilogram$^{-1}$ and about 10 milligram×kilogram$^{-1}$ body weight of a mammal. An even more preferred single dose of a TGFβ-regulating agent comprises between about 5 microgram× kilogram$^{-1}$ and about 7 milligram×kilogram$^{-1}$ body weight of a mammal. An even more preferred single dose of a TGFβ-regulating agent comprises between about 10 microgram×kilogram$^{-1}$ and about 5 milligram×kilogram$^{-1}$ body weight of a mammal. A particularly preferred single dose of a TGFβ-regulating agent comprises between about 0.1 milligram×kilogram$^{-1}$ and about 5 milligram× kilogram$^{-1}$ body weight of a mammal, if the a TGFβ-regulating agent is delivered by aerosol. Another particularly preferred single dose of a TGFβ-regulating agent comprises between about 0.1 microgram×kilogram$^{-1}$ and about 10 microgram×kilogram$^{-1}$ body weight of a mammal, if the a TGFβ-regulating agent is delivered parenterally.

In another embodiment, a TGFβ-regulating agent of the present invention can be administered simultaneously or sequentially with a compound capable of enhancing the ability of a TGFβ-regulating agent to protect a mammal from a disease involving inflammation. The present invention also includes a formulation containing a TGFβ-regulating agent and at least one such compound to protect a mammal from a disease involving inflammation. A preferred compound to be administered simultaneously or sequentially with a TGFβ-regulating agent includes, including but is not limited to, any anti-inflammatory agent. According to the present invention, an anti-inflammatory agent can be any compound which is known in the art to have anti-inflammatory properties, and can also include any compound which, under certain circumstances and/or by being administered in conjunction with a TGFβ-regulating agent, can provide an anti-inflammatory effect. A suitable compound to be administered simultaneously or sequentially with a TGFβ-regulating agent includes a compound that is capable of regulating IgE production (i.e., suppression of interleukin-4 induced IgE synthesis), regulating interferon-gamma production, regulating NK cell proliferation and activation, regulating lymphokine activated killer cells (LAK), regulating T helper cell activity, regulating degranulation of mast cells, protecting sensory nerve endings, regulating eosinophil and/or blast cell activity, preventing or relaxing smooth muscle contraction, reduce microvascular permeability and Th1 and/or Th2 T cell subset differentiation. A preferred anti-inflammatory agent to be administered simultaneously or sequentially with a TGFβ-regulating agent includes, but is not limited to, an antigen, an allergen, a hapten, proinflammatory cytokine antagonists (e.g., anti-cytokine antibodies, soluble cytokine receptors), proinflammatory cytokine receptor antagonists (e.g., anti-cytokine receptor antibodies), anti-CD23, anti-IgE, anticholinergics, immunomodulating drugs, leukotriene synthesis inhibitors, leukotriene receptor antagonists, glucocorticosteroids, steroid chemical derivatives, anti-cyclooxygenase agents, anti-cholinergic agents, beta-adrenergic agonists, methylxanthines, anti-histamines, cromones, zyleuton, anti-CD4 reagents, anti-IL-5 reagents, surfactants, anti-thromboxane reagents, anti-serotonin reagents, ketotiphen, cytoxin, cyclosporin, methotrexate, macrolide antibiotics, heparin, low molecular weight heparin, and mixtures thereof. The choice of compound to be administered in conjunction with a TGFβ-regulating agent can be made by one of skill in the art based on various characteristics of the mammal. In particular, a mammal's genetic background, history of occurrence of inflammation, dyspnea, wheezing upon physical exam, symptom scores, physical signs (i.e., respiratory rate), exercise tolerance, use of rescue medication (i.e., bronchodialators) and blood gases.

A formulation of the present invention can also include other components such as a pharmaceutically acceptable excipient. For example, formulations of the present invention can be formulated in an excipient that the mammal to be protected can tolerate. Examples of such excipients include water, saline, phosphate buffered solutions, Ringer's solution, dextrose solution, Hank's solution, polyethylene glycol-containing physiologically balanced salt solutions, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability or buffers. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a TGFβ-regulating agent or a formulation of the present invention can include a controlled release composition that is capable of slowly releasing the TGFβ-regulating agent or formulation of the present invention into a mammal. As used herein a controlled release composition comprises a TGFβ-regulating agent or a formulation of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, dry powders, and transdermal delivery systems. Other controlled release compositions of the present invention include liquids that, upon administration to a mammal, form a solid or a gel in situ. Preferred controlled release compositions are biodegradable (i.e., bioerodible).

A preferred controlled release composition of the present invention is capable of releasing a TGFβ-regulating agent or a formulation of the present invention into the blood of a mammal at a constant rate sufficient to attain therapeutic dose levels of a TGFβ-regulating agent or the formulation to prevent inflammation over a period of time ranging from days to months based on TGFβ-regulating agent toxicity parameters. A controlled release formulation of the present invention is capable of effecting protection for preferably at least about 6 hours, more preferably at least about 24 hours, and even more preferably for at least about 7 days.

Isolated nucleic acid molecules to be administered in a method of the present invention include: (a) recombinant molecules useful in the method of the present invention in a non-targeting carrier (e.g., as "naked" DNA molecules, such as is taught, for example in Wolff et al., 1990, *Science* 247, 1465–1468); and (b) recombinant molecules of the present invention complexed to a delivery vehicle of the present invention. Particularly suitable delivery vehicles for local administration comprise liposomes, viral vectors and ribozymes. Delivery vehicles for local administration can further comprise ligands for targeting the vehicle to a particular site. Preferably, a nucleic acid molecule encoding a TGFβ1 protein is administered by a method which includes, intradermal injection, intramuscular injection, intravenous injection, subcutaneous injection, or ex vivo administration.

In one embodiment, a recombinant nucleic acid molecule useful in a method of the present invention is injected directly into muscle cells in a patient, which results in prolonged expression (e.g., weeks to months) of such a recombinant molecule. Preferably, such a recombinant molecule is in the form of "naked DNA" and is administered by direct injection into muscle cells in a patient. In other embodiments, a recombinant nucleic acid molecule useful in a method of the present invention is delivered to a patient by inhaled routes in the form of, for example, powders, liquids, emulsions, or aerosols. Methods of inhaled delivery are well known in the art.

A pharmaceutically acceptable excipient which is capable of targeting is herein referred to as a "delivery vehicle." Delivery vehicles of the present invention are capable of delivering a formulation, including a TGFβ1 protein and/or a nucleic acid molecule encoding a TGFβ1 protein, to a target site in a mammal. A "target site" refers to a site in a mammal to which one desires to deliver a therapeutic formulation. For example, a target site can be any cell which is targeted by direct injection or delivery using liposomes, viral vectors or other delivery vehicles, including ribozymes. Examples of delivery vehicles include, but are not limited to, artificial and natural lipid-containing delivery vehicles, viral vectors, and ribozymes. Natural lipid-containing delivery vehicles include cells and cellular membranes. Artificial lipid-containing delivery vehicles include liposomes and micelles. A delivery vehicle of the present invention can be modified to target to a particular site in a mammal, thereby targeting and making use of a nucleic acid molecule at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

One preferred delivery vehicle of the present invention is a liposome. A liposome is capable of remaining stable in a mammal for a sufficient amount of time to deliver a nucleic acid molecule described in the present invention to a preferred site in the mammal. A liposome, according to the present invention, comprises a lipid composition that is capable of delivering a nucleic acid molecule described in the present invention to a particular, or selected, site in a mammal. A liposome according to the present invention comprises a lipid composition that is capable of fusing with the plasma membrane of the targeted cell to deliver a nucleic acid molecule into a cell. Suitable liposomes for use with the present invention include any liposome. Preferred liposomes of the present invention include those liposomes standardly used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule of the present invention can be achieved using methods standard in the art.

Another preferred delivery vehicle comprises a recombinant virus particle vaccine (i.e., viral vector). A recombinant virus particle vaccine of the present invention includes a recombinant nucleic acid molecule useful in the method of the present invention, in which the recombinant molecules are packaged in a viral coat that allows entrance of DNA into a cell so that the DNA is expressed in the cell. A number of recombinant virus particles can be used, including, but not limited to, those based on alphaviruses, poxviruses, adenoviruses, herpesviruses, arena virus and retroviruses. An example of an adenovirus viral vector useful in the method of the present invention is set forth in the examples section.

Also included in the present invention are therapeutic molecules known as ribozymes. A ribozyme typically contains stretches of complementary RNA bases that can base-pair with a target RNA ligand, including the RNA molecule itself, giving rise to an active site of defined structure that can cleave the bound RNA molecule (See Maulik et al., 1997, supra). Therefore, a ribozyme can serve as a targeting delivery vehicle for the nucleic acid molecule encoding TGFβ, or alternatively, the ribozyme can target and bind to RNA encoding a TGFβ protein, and thereby effectively inhibit the translation of the TGFβ protein. Of particular interest in the present invention are ribozymes targeted against RNA encoding TGFβ2 and/or TGFβ3.

Another embodiment of the present invention comprises a method for prescribing treatment for a respiratory disease involving an inflammatory response, the method comprising: (1) administering to a mammal a TGFβ-regulating agent; (2) measuring a change in lung function in response to a provoking agent in the mammal to determine if the TGFβ-regulating agent is capable of modulating airway hyperresponsiveness; and (3) prescribing a pharmacological therapy effective to reduce inflammation based upon the changes in lung function. A change in lung function includes measuring static respiratory function before and after administration of a TGFβ-regulating agent. In accordance with the present invention, the mammal receiving the TGFβ-regulating agent is known to have a respiratory disease involving inflammation. Measuring a change in lung function in response to a provoking agent can be done using a variety of techniques known to those of skill in the art. In particular, a change in lung function can be measured by determining the $FEV_1$, $FEV_1/FVC$, $PC_{20methacholine}FEV_1$, post-enhanced pause (Penh), conductance, dynamic compliance, lung resistance ($R_L$), airway pressure time index (APTI), and/or peak flow for the recipient of the provoking agent. Such methods are known in the art. Other methods to measure a change in lung function include, for example, airway resistance, dynamic compliance, lung volumes, peak flows, symptom scores, physical signs (i.e., respiratory rate), wheezing, exercise tolerance, use of rescue medication (i.e., bronchodialators) and blood gases. A suitable pharmacological therapy effective to reduce inflammation in a mammal can be evaluated by determining if and to what extent the administration of a TGFβ-regulating agent has an effect on the lung function of the mammal. If a change in lung function results from the administration of a TGFβ-regulating agent, then that mammal can be treated with the TGFβ-regulating agent. Depending upon the extent of change in lung function, additional compounds can be administered to the mammal to enhance the treatment of the mammal. If no change or a sufficiently small change in lung function results from the administration of the TGFβ-regulating agent, then that mammal should be treated with an alternative compound to the TGFβ-regulating agent. The present method for prescribing treatment for a respiratory disease can also include evaluating other characteristics of the patient, such as the patient's history of respiratory disease, the presence of infectious agents, the patient's habits (e.g., smoking), the patient's working and living environment, allergies, a history of life threatening respiratory events, severity of illness, duration of illness (i.e., acute or chronic), and previous response to other drugs and/or therapy.

Another embodiment of the present invention comprises a method for monitoring the success of a treatment for a respiratory disease involving an inflammatory response in a mammal, the method comprising: (1) administering a TGFβ-regulating agent for a respiratory disease involving an inflammatory response; (2) measuring a change in the lung function of the mammal in response to a provoking agent of the present invention; and (3) monitoring the success of the treatment by comparing the change in lung function with previous measurements of lung function in the mammal. If the treatment does not result in the improvement of lung function, then the administration of the TGFβ-regulating agent should be able to alter lung function. Conversely, if the treatment does result in lung function improvement, then the administration of the TGFβ-regulating agent should not alter lung function because the lung function will have been improved by the original treatment. The monitoring of success can also include comparing the change in lung function before and after administration of the TGFβ-regulating agent to a mammal with other aforementioned characteristics of the mammal.

Another embodiment of the present invention includes a method for long-term care of a patient having a disease involving inflammation, the method comprising: (1) assessing the status of the disease of a patient; (2) administering to the patient a TGFβ-regulating agent; and (3) providing long-term care of the patient by preventing significant exposure of the patient to the cause of the disease. Preferably, the status of the disease is assessed by determining a characteristic of the disease, such as determining the form, severity and complications of the disease. In addition, the status of the disease is assessed by determining, for example, a causative agent and/or a provoking agent of the disease. From the assessment of the causative and/or provoking agent of the disease, long-term care can be provided by minimizing the exposure of the patient to the causative and/or provoking agent of the disease.

The following examples are provided for the purposes of illustration and are not intended to limit the scope of the present invention.

EXAMPLES

Example 1

The following example characterizes the murine system of antigen-driven hyperresponsiveness of the present invention.

Mammal models of disease are invaluable to provide evidence to support a hypothesis or justify human experiments. Mice have many proteins which share greater than 90% homology with corresponding human proteins. The present inventors have developed an antigen-driven murine system that is characterized by an immune (IgE) response, a dependence on a Th2-type response, and an eosinophil response. Pathologically the most impressive chronic change is the fibrotic remodeling of the airway wall. More importantly, the model is characterized by both a marked and evolving hyperresponsiveness of the airways.

The development of a versatile murine system of chronic aeroantigen exposure, which is associated with profound eosinophilia and marked, persistent and progressive airways hyperresponsiveness, provides an unparalleled opportunity to investigate the mechanisms of excessive airways narrowing. The mouse system described herein is characterized by significant eosinophilia, followed by airway fibrosis and collagen deposition. The present inventors have used the mouse system to provide evidence which link airways fibrosis to airways dysfunction and to determine the role of TGFβ in orchestrating airways fibrosis. Lastly, the mouse system is useful to determine structure-function relationships and the physiologic mechanisms which account for the marked airway hyperresponsiveness. Use of the mouse system of the present invention will lead to a better insight into the pathogenesis of excessive airways narrowing and fixed airflow limitation observed in asthma.

Mice mount an IgE response after intraperitoneal sensitization with ovalbumin (OVA). BALB/c mice were immunized intraperitoneally with 10 µg OVA in 100 µg $Al(OH)^3$ dissolved in phosphate buffered saline (PBS). The mice were then chronically exposed (i.e., challenged) for 8 days (i.e., 8 exposures of 30 minutes each in 8 days) to 1% aerosolized OVA. It should be noted that both immunization and subsequent antigen challenge are required to observe a response in mice.

To characterize the murine model, pulmonary function measurements of airway resistance ($R_L$) and dynamic compliance ($C_L$) and hyperresponsiveness were obtained. Mice were anesthetized with pentobarbital (e.g., 70 mg/kg of intraperitoneal pentobarbital sodium), and the trachea and right internal jugular vein were exposed. A metal 19 gauge endotracheal catheter was inserted and sutured into the trachea, and a 0.0048 cm internal diameter×5 cm Silastic catheter (Dow Corning Corp., Midland, Mich.) was inserted and sutured into the right internal vein. Following surgery, the mice were in a plethysmographic chamber and the tracheostomy tube was attached to a 4-way connector (Small Parts, Inc., Miami Lakes, Fla.), with one port connected to a catheter measuring airway opening pressure ($P_{AO}$) and two ports connected to the inspiratory and expiratory ports of a volume cycled ventilator (Harvard Apparatus Rodent Ventilator, Model 680, South Natwick, Mass.). The mice were ventilated at 200 breaths per minute, tidal volume of 5–6 ml/kg, and with 2 cm $H_2O$ positive end-expiratory pressure. Adequacy of alveolar ventilation was confirmed by the lack of spontaneous respiration (i.e., over-breathing), and transcutaneous $CO_2$ measurements. Transpulmonary pressure was estimated as the $P_{AO}$, referenced to pressure within the plethysmographic using a differential pressure transducer (Validyne Model MP-45-1-871, Validyne Engineering Corp., Northridge, Calif.). Changes in volume were determined by pressure changes in the plethysmographic chamber referenced to pressure in a reference box using a second differential pressure transducer. The two transducers and amplifiers were electronically phased to less than 5 degrees from 1 to 30 Hz and then converted from an analog to digital signal using a 16 bit analog to digital board Model NB-MIO-16X-18 (National Instruments Corp., Austin, Tex.) at 600 bits per second per channel. The digitized signals were fed into a Macintosh Quadra 800 computer (Model M1206, Apple Computer, Inc., Cupertino, Calif.) and analyzed using the real time computer program LabVIEW (National Instruments Corp., Austin, Tex.). Flow was determined by differentiation of the volume signal and compliance was calculated as the change in volume divided by the change in pressure at zero flow points for the inspiratory phase and expiratory phase. Average compliance was calculated as the arithmetic mean of inspiratory and expiratory compliance for each breath. The LabVIEW computer program used pressure, flow, volume and average compliance to calculate pulmonary resistance (Rl) and compliance according to the method of Amdur et al. (pp. 364–368, 1958, *Am. J. Physiol.*, vol. 192). The breath by breath results for Rl, compliance, conductance and specific compliance were tabulated and the reported values are the average of at least 10–20 breaths at the peak of response for each dose.

Following placement in a plethysmographic chamber, each mouse was challenged with methacholine to assess airway hyperresponsive pulmonary function. In vivo airway hyperresponsiveness (AHR) was assessed as the change in respiratory system function after noncumulative, intravenous methacholine (i.e., Acetyl-β-methylcholine) challenge (See FIG. 2). Acetyl-β-methylcholine (Aldrich Chemical, Milwaukee, Wis.) was dissolved in normal saline and administered into the internal jugular vein catheter with a micro syringe (Hamilton, Co., Reno, Nev.). AHR was assessed as the resistance ($R_L$) in $cmH_2O$/ml/sec following administration of 6 tripling doses of about 5 µg/mg to about 1233 µg/mg of intravenous methacholine.

Figure 2:
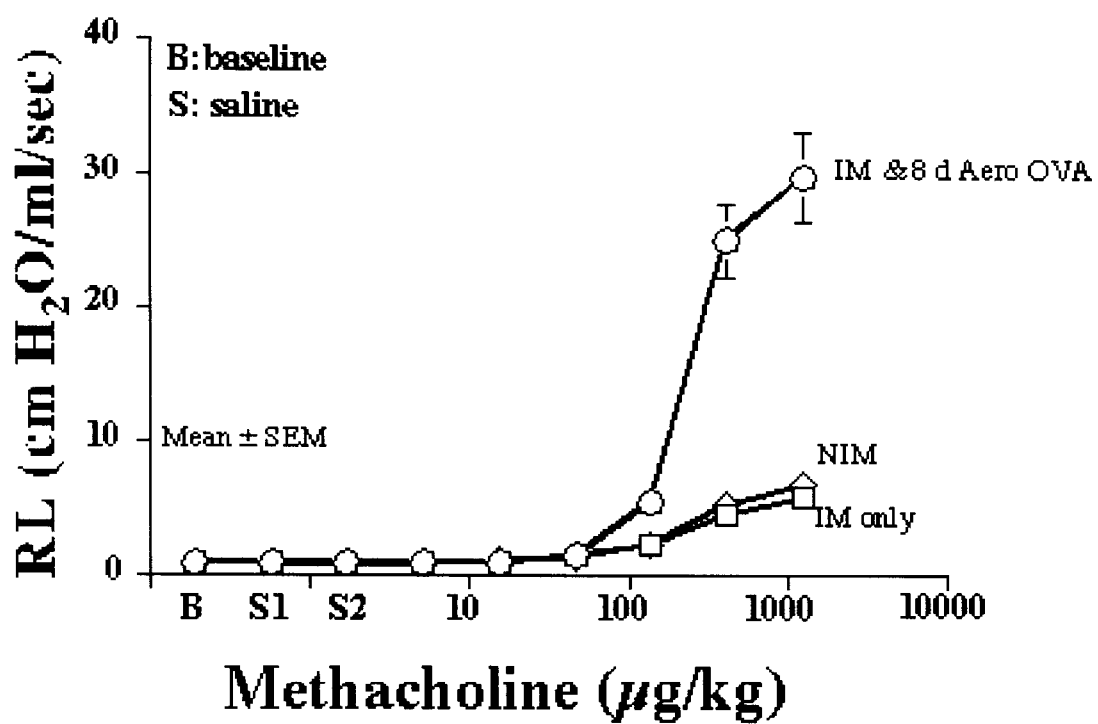
FIG. 2 is a line graph showing dose-response curves of pulmonary resistance to intravenous methacholine.
Figure 3:
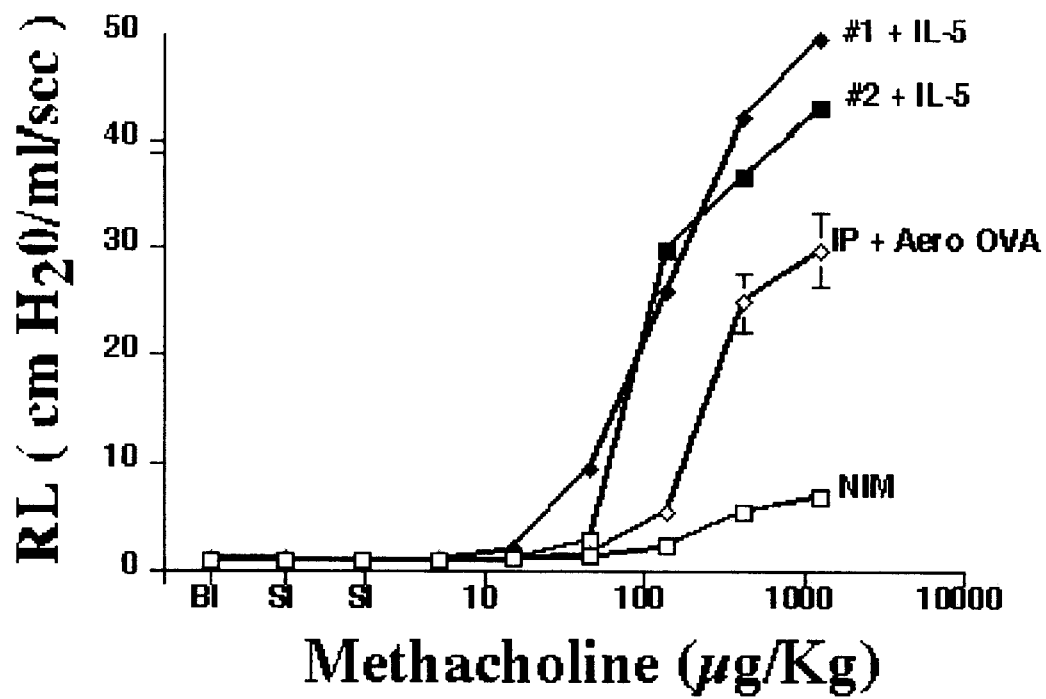
FIG. 3 is a line graph illustrating dose-response curves of pulmonary resistance to aerosolized methacholine.

The means and standard errors of the log 10 of resistance ($R_L$) by dose of methacholine and by group obtained from the stress test are illustrated in FIG. 2 (intravenous methacholine injections) and FIG. 3 (aerosolized methacholine) (n=the number of mice in each treatment group). It should be noted that measuring the $R_L$ value in a mouse, can be used to diagnose airflow obstruction similar to measuring the $FEV_1$ and/or $FEV_1/FVC$ ratio in a human.

FIG. 2 shows dose-response curves of acute (24 hour) pulmonary resistance ($R_L$) to intravenous methacholine. The mean±SEM is shown; points without SEM have variability ≦the plot token. Non-immune mice (NIM) are shown as triangles (n=7); immunized only mice (IM) are shown as squares; and mice which are immunized and exposed to aerosolized ovalbumin (IM & 8d Aero OVA) are shown as circles (n=7).

FIG. 2 demonstrates that airway responsiveness to methacholine is shifted several logs to the left and the magnitude of maximal resistance ($Rl_{max}$) generated at the highest dose of methacholine was increased well over four times the baseline values, indicating excessive airways narrowing. Baseline resistance is not elevated at this timepoint. Immunized but not challenged animals (IM) were similar to control non-immune animals. These shifts in methacholine responsiveness and $Rl_{max}$ are similar in magnitude to changes seen in human asthmatics. This response is antigen-specific because when mice are immunized to OVA but challenged with an irrelevant antigen (ragweed), they do not develop airways hyperresponsiveness (data not shown).

Example 2

The following example demonstrates the relevance of the murine model of airways hyperresponsiveness to current concepts of asthma pathogenesis.

In these experiments, total serum IgE/IgG levels in the mice used in Example 1 were measured and the presence of Th2 paradigm as well as the role of the eosinophil were investigated. Total IgE levels for nonimmune mice (1.85±0.18 µg/ml), immunized mice (1.20±0.24), and mice receiving aerosolized OVA without immunization (1.7±0.23 µg/ml) were similar, but total IgE levels increased in immunized challenged animals (3.53±0.29). Antigen specific IgE, and antigen-specific IgG were also elevated. This hyperresponsiveness appears to be IgE, B cell independent (data not shown).

The role of Th1/Th2 cells was also investigated in this murine model by first immunizing the animals with complete Freunds adjuvant, an adjuvant known to cause a Th1-type response prior to induction of antigen-dependent hyperresponsiveness as described in Example 1. Animals immunized with complete Freunds adjuvant failed to show eosinophilia or increased airways hyperresponsiveness (data not shown).

Next, the role of a Th2-type response was investigated by attempting to "switch" the T cell response to a Th1-type response by administering IL-12 intranasally during the aerosol antigen challenge. IL-12 is a cytokine which is known to influence a Th1-type response. Both the eosinophilic influx and increase in responsiveness were blocked (data not shown).

To investigate the role of eosinophils in this murine model, fluorescent immunochemistry was performed with a eosinophil MPB antibody on lung sections of both non-immune and immunized, antigen challenged mice. Mice immunized and challenged as described in Example 1 showed an influx of eosinophils in the lung and bronchoalveolar sections (data not shown). At 4 days of antigen challenge, eosinophils (EOS) were 5% of $10 \times 10^4$ white blood cells (WBC)/ml, rising to 30–40% of the total cells in the bronchoalveolar lung (BAL) ($40 \times 10^4$ WBC/ml) by 8 days of antigen challenge (data not shown). This lung eosinophilia is under leukotriene and IL-5 control. IL-5 is taken as a marker for Th2 lymphocytes, is elevated in asthma, is capable of eosinophil recruitment, and activates eosinophils.

The next experiment determined whether IL-5 would further up-regulate airway dysfunction and lend support to the Th2 response and apparent role for eosinophils in this model. FIG. 3 illustrates dose-response curves of pulmonary resistance ($R_L$) to intratracheal methacholine. Data for non-immune mice (NIM) and IP+Aero OVA mice are the same data as shown in FIG. 2. Mouse #1 and Mouse #2 were treated with 125U of rIL-5 intratracheally 24 hours prior to the last antigen challenge. At day 8 of aerosolized OVA exposure (n=2), 125U (25 μl) of recombinant murine IL-5 was intratracheally instilled.

IL-5 caused a marked increase in responsiveness, and a lavage showed higher numbers of eosinophils. In addition, an antibody against IL-5 (TRFK5) blocks this response.

Example 3

The following example shows the dependency of airways hyperresponsiveness in the murine model on antigen exposure.

Figure 4:
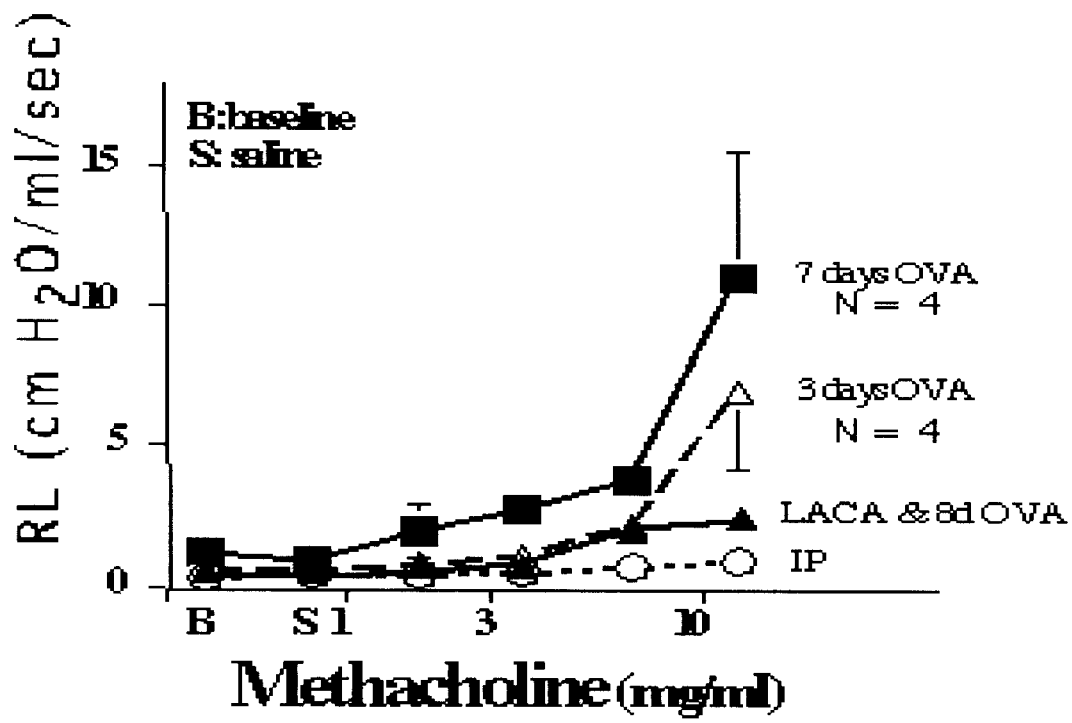
FIG. 4 is a line graph showing dose-dependent, antigen-induced airways hyperresponsiveness.

Severity of the physiologic response to antigen is known to be dose-dependent presumably due to a dose-dependent increase in inflammation. The dependency of airways hyperresponsiveness on antigen was investigated by exposing animals to 3 days (3d) or 7 days (7d) of antigen exposure. Airways responsiveness was measured with inhaled methacholine as described above. FIG. 4 shows the results of this experiment (open triangles and squares).

As can be appreciated, the increase in airways hyperresponsiveness to 3 and 7 days of OVA exposures was antigen dose-dependent. The inflammatory response of the eosinophilia in the lavage also shows dose-dependent changes as assessed by lavage, morphometrics and lung digests (data not shown).

Example 4

The following example shows that antigen-driven airways hyperresponsiveness induces persistent changes in airways responsiveness over time.

Figure 5:
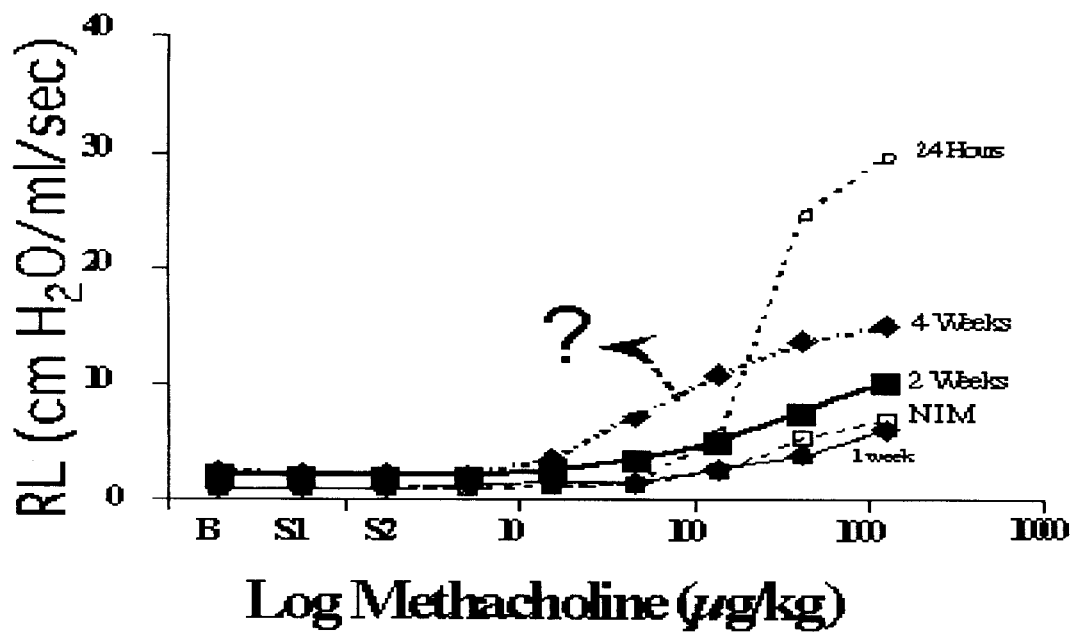
FIG. 5 is a line graph illustrating progressive, antigen-induced hyperresponsiveness to intravenous methacholine.

Given the severity of physiologic response, the possibility that persistent changes had occurred was explored. Groups (n=2) of animals were immunized with OVA and challenged for 8 days with OVA. Responsiveness was measured at 1, 2 and 4 weeks following the last challenge. FIG. 5 shows the dose-response curves to intravenous methacholine at 1 week (n=2), 2 weeks (n=2), and 4 weeks (n=2). At 1 week post challenge, the dose response curve has returned to within normal range, however, at 2 and 4 weeks post chronic antigen challenge there is progressive increase in hyperresponsiveness. And while the peak increase in resistance is less, there is now a remarkable and a progressive shift leftwards of the dose-response curve (NB: the log scale). The baseline resistance is also higher (data not shown).

The temporal progression and apparent shape of the dose-response curves suggest the possibility that very different mechanisms are operational acutely (±24 hours) in contrast to chronically (2–4 weeks). It is possible that transient inflammation accounts for the acute response, whereas a progressive fibroproliferative process of a sequence of fibrotic events or collagen maturation accounts for the chronic effects.

Example 5

The following example illustrates the pathogenic alterations which take place in the lungs of mice in the murine model for antigen-driven airways hyperresponsiveness.

To investigate the pathogenic alterations in the present model, tissue was obtained at 24 hours and at 4 weeks following aerosol antigen challenge. Sections were stained with Sirius red, which stains collagen a bright red, and immunocytochemistry was performed with antibodies against type I and III collagen.

Striking increases in collagen were found as evidenced by the increase in red staining structures (data not shown) and a thicker airway wall. Light polarization revealed increased birefringence at 24 hours and at 4 weeks post antigen challenge, which suggests new collagen synthesis. In addition, at both 24 hours and 4 weeks post challenge, increased basement membrane and wall thickness and disorganized collagen deposition was observed. Initially collagen was not deposited in a uniform fashion. This disordered collagen deposition in the subepithelium may have important significance to explaining the uncoupling of airways (i.e., parenchyma and loss of elastic recoil) observed especially at chronic time points.

Immunocytochemistry staining for type I and III collagen showed increased collagen deposition in the walls of small lobar airways (data not shown). Comparison of acute (48 hour) to chronic (4 week) sections showed increased collagen. In addition, at 4 weeks type I collagen was more apparent, which is consistent with the changes observed in dermal wound healing.

Figure 6:
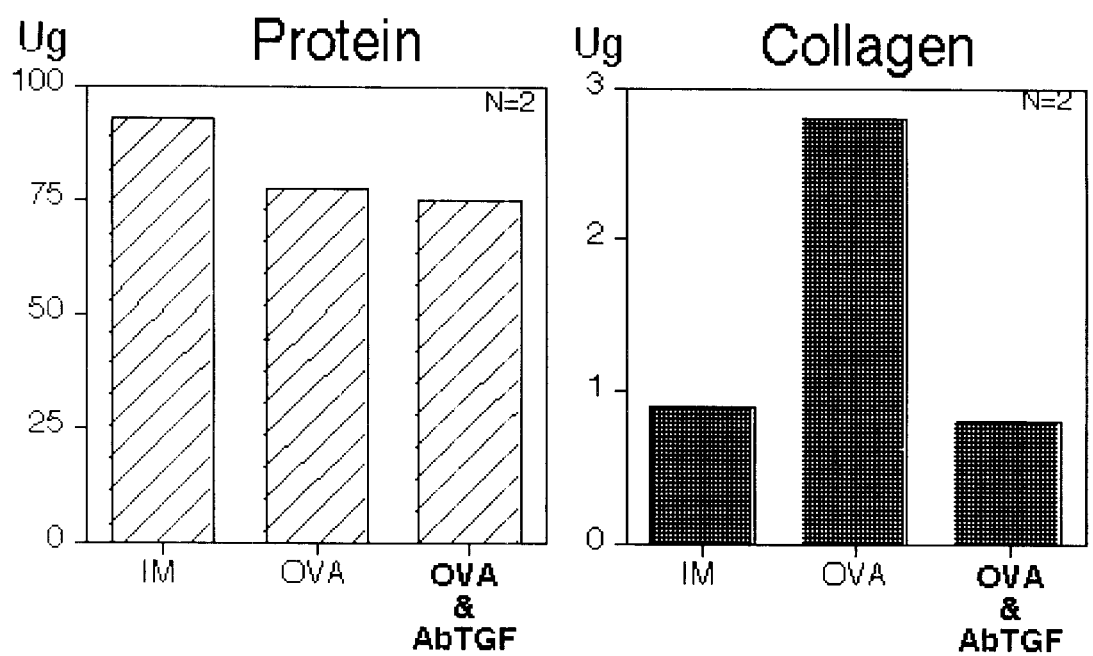
FIG. 6 is a bar graph showing a Picrosirius determination of protein and collagen content in lung sections.

Sections stained with picric acid, sirius red and fast green (picrosirius) were then extracted to determine the total collagen present (FIG. 6). FIG. 6 shows a Picrosirius determination of protein (left hand panel) and collagen (right hand panel) content in lung sections (IM: animals immunized and not exposed (N=2); OVA: animals immunized and antigen exposed (N=2); OVA+AdTGF: OVA exposed but treated with neutralizing antibody to TGFβ (N=2)). There was a marked (3-fold) increase in collagen deposition. The results using antibody to TGFβ are discussed in Example 6.

Taken together, these preliminary findings indicate that antigen challenge leads to progressive airway fibrosis, quantifiable deposition of collagen and a functional role of collagen deposition in airways hyperresponsiveness.

Example 6

The following example shows that TGFβ plays a direct role in asthma.

Figure 7:
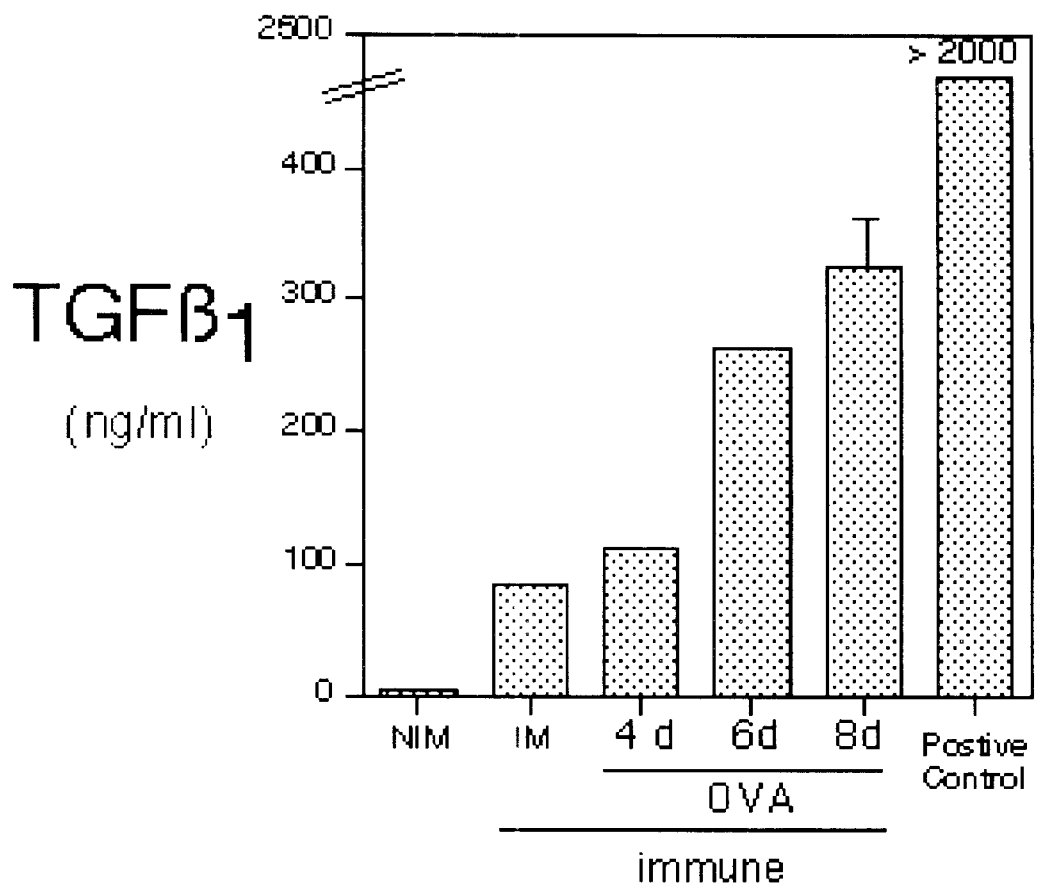
FIG. 7 is a bar graph illustrating TGFβ1 levels in BAL from non-immune, immune, and 4, 6 and 8 day antigen-challenged mice.

In this experiment, TGFβ1 was measured in the lavage from non-immune mice and immune and OVA treated mice. In addition, a neutralizing antibody was used to block the action of TGFβ. A preliminary study utilizing a TGFβ1 ELISA array showed low TGFβ1 in immune unchallenged animals and a dose-dependent rise in TGFβ1 with increasing days of antigen-exposure (FIG. 7). FIG. 7 illustrates preliminary results of TGFβ1 levels in BAL from non-immune mice (NIM) (pooled N=3), immune mice (IM) not challenged, and immune mice receiving 4, 6 and 8 days of antigen exposure (Day 8 N=4). Lavage from a rat infected with Ad5r TGFβ1 (adenoviral vector containing TGFβ1) served as a positive control. These data suggest that a rise in TGFβ occurs early in the airways response. To assess the effect of a blocking antibody against TGFβ (pan-specific antibody which binds to all three known isoforms of TGFβ), four groups of mice were studied: immunized (IM: N=2); immunized and challenged with 8 days of aerosolized antigen (OVA N=3); antibody treated with pre-immune rabbit IgG serum (N=3) and antibody treated with OVA and anti-TGFβ (OVA+AbTGF N=3). Antibody treated animals were administered 25 μg in 25 μl of a pan-specific neutralizing antibody to TGFβ (specific for all isoforms of (TGFβ), intranasally. Pre-immune rabbit IgG and a lower dose of the antibody (2.5 μg—data not shown) served as controls, neither of which altered responsiveness.

Figure 8:
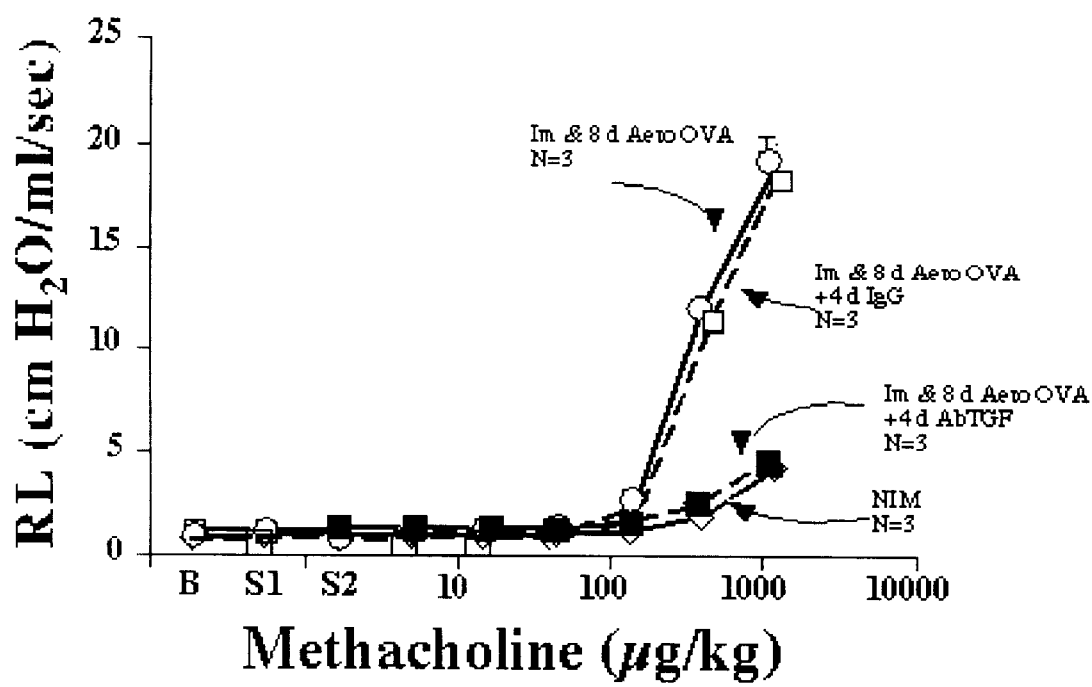
FIG. 8 is a line graph showing a blocking of airway hyperresponsiveness by antibody against TGFβ.

FIG. 8 shows the results of this experiment. The animals treated with the antibody to TGFβ showed airways responsiveness similar to the negative controls (i.e., the response is blocked). A lavage still showed elevations in eosinophil numbers (data not shown), but histologic examination failed to show collagen deposition and airway wall thickening (data not shown). Quantitatively, the increase in collagen content (picrosirius) was also blocked (FIG. 6). Treatment with the preimmune rabbit IgG did not alter responsiveness (i.e., same response as immunized, OVA challenged animals). Since the antibody was given only for the first 4 days of the 8 day exposure, this data indicates that TGFβ signaling occurs early in the process.

Example 7

The following example demonstrates the validity of using adenovirus vectors as a means of manipulating the murine antigen-driven airways hyperresponsiveness system.

To investigate the validity of using an adenovirus vector system to generate TGFβ1 within the airway wall, the following pilot experiments were performed. Mice (N=2) were given an intranasal injection of 1×10$^8$ pfu Ad5LacZ (an adenovirus vector carrying the LacZ gene). Lungs from the mice were fixed and processed to locate the reporter gene LacZ. At 60 hours after infection with the viral vector, LacZ was found in the epithelium or the mouse airways (data not shown). Significant gene presence was still seen at day 14 (data not shown).

Figure 9:
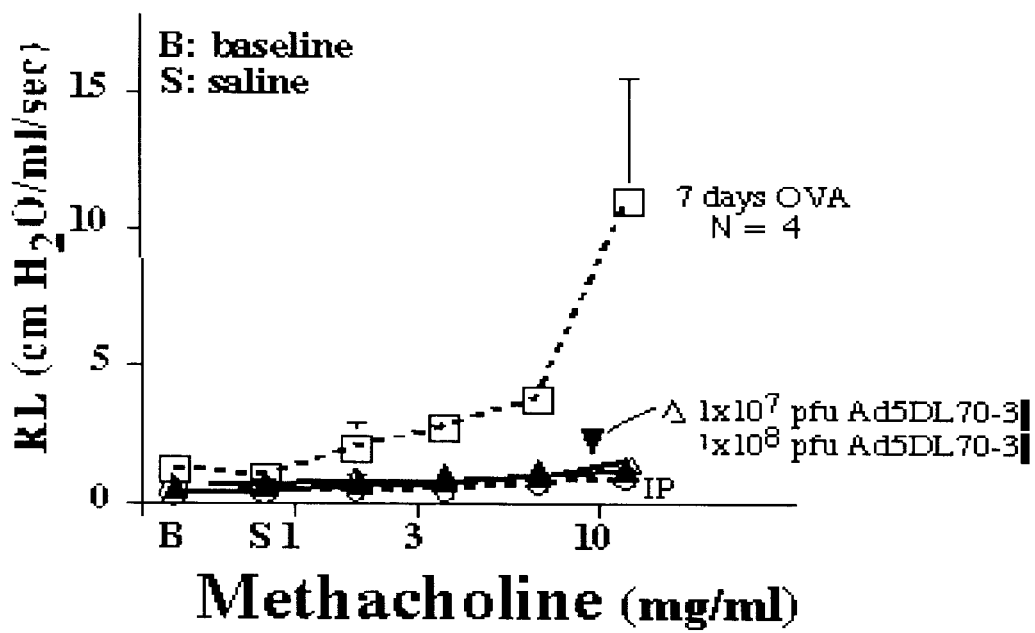
FIG. 9 is a line graph illustrating the effect of empty adenovirus infection on responsiveness.

Animals were then infected with an empty, but replication-deficient virus (Ad5r DL70-3), and studied as a model of airway hyperresponsiveness as previously described. FIG. 9 illustrates the effect of empty adenovirus infection on responsiveness. At one and three weeks prior to the methacholine exposure, mice (N=4) were infected with 1×10$^7$ or 10$^8$ pfu of the AdDL70-3 vector. Negative controls (IP) and positive controls (OVA immunized mice challenged with 7d OVA) were included. The animals infected with Ad5r DL70-3 were not hyperresponsive at one week (data not shown) or at three weeks (FIG. 9). There was no apparent change in lavage cell numbers.

These data suggest these adenovirus vectors will be an excellent means of manipulating this system. In further support, gene transfer using these vectors with IL-5 and IL-4 genes completely reconstitute antigen responses in IL5 KO and IL4 KO mice. Those data also suggest that these viral vectors do not alter antigen responses per se. Taken together, these experiments show that 1) adenovirus infections do not change airways responsiveness or the response to antigen, and 2) TGFβ is required to observe airway wall remodeling, collagen deposition and hyperresponsiveness.

In summary, the present inventors have developed a versatile and germane murine system of antigen-induced airways dysfunction. The system is characterized by marked (>2 log shift) hyperresponsiveness and loss of plateau; eosinophilia (which plays a functional role in hyperresponsiveness); dose-dependent response to antigen; and a temporal progression of hyperresponsiveness. Airway fibrosis due to collagen deposition is prominent. The present inventors also demonstrate herein a mechanistic link between collagen deposition and airways dysfunction and a role for TGFβ in such collagen deposition. Mechanistically, the increase in airways responsiveness appears not to be due to increased ASM contractility but is rather due to alterations in peripheral responsiveness, a mechanical uncoupling by airways to the parenchyma, and a loss of elastic recoil.

The present inventors have shown that chronic antigen exposure in immunized animals of specific murine strains leads to chronic and progressive increases in airways hyperresponsiveness. These animals also appear to develop progressive airflow limitation. Histological inspection of the airways reveals a marked, persistent deposition of collagen—the airway is remodeled and assays of collagen/protein content demonstrate quantitative increase in collagen deposition. Interruption of inflammatory processes by blockade of the effects of TGFβ or collagen secretion are associated with an absence of collagen deposition and a failure to develop hyperresponsiveness. Taken together, these data demonstrate that eosinophilic inflammation and the generation of growth factor results in a progressive fibroproliferative process characterized by collagen deposition and a progressive fibrotic remodeling of the airway wall.

Example 8

The following example demonstrates the effects of TGFβ blockade on the chronic effects of antigen challenge.

Figure 10:
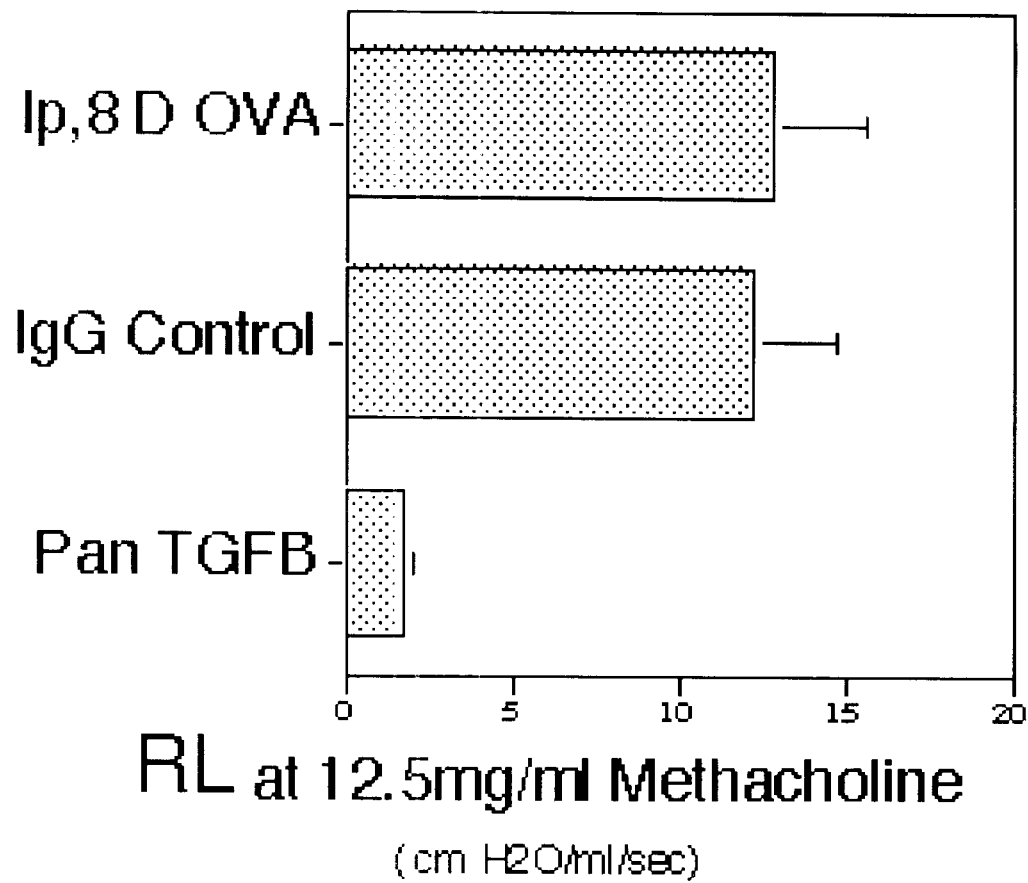
FIG. 10 is a bar graph illustrating the effect of pan-specific TGFβ antibody in late or chronic airways responsiveness.

Three groups of mice were immunized and then challenged with 8 days of aerosol OVA as described in Example 1. One group of mice was treated with a pan-specific antibody to TGFβ (N=4) and one group was treated with rabbit IgG (N=2) as an isotype control. Antibody treatment occurred during the first focused days of antigen exposure. The mice were tested (as described in Example 1) 30 days after antigen challenge. FIG. 10 shows that the pan-specific antibody to TGFβ blocked the alterations in responsiveness to antigen exposure even 30 days after treatment (i.e., chronic effects).

Example 9

The following example demonstrates the feasibility of using heterozygote TGFβ1 (+/−) mice in further experiments to manipulate and explore the role of TGFβ isoforms in airway hyperresponsiveness.

C57BL/6 mice that are heterozygous for the TGFβ1 gene (+/−; C57BL/6J-tgfbl tml Doc−) and wild-type (+/+) controls were obtained from JAX Labs. The mice were tested for antigen-driven airways hyperresponsiveness as described in Example 1 (data not shown). Since the genetic background of the heterozygous mice is C57BL/6 (i.e., an airways hyperresponsiveness resistant strain), only a modest increase in $R_L$ in response to antigen was observed in the wild-type control mice, but the TGFβ1 +/− mouse showed a slightly enhanced response. At a dose of 50 mg/ml of methacholine, the $R_L$ response was 1.84±1.1 cmH$_2$O/ml/sec in TGFβ1 +/+ mice versus 3.3±0.9 in the TGFβ1 +/− heterozygote. These results indicate that partial loss of TGFβ1 enhances airways hyperresponsiveness.

These experiments demonstrate the feasibility of using heterozygote animals to manipulate the murine system. To increase the antigen response of control mice, either the antigen immunization procedure can be changed or an airways hyperresponsiveness agonist can be introduced. Alternatively, the heterozygote can be backcrossed onto a BALB/c background over about 6 generations.

Example 10

The following example demonstrates that excess TGFβ1 isoform does not increase airways responsiveness.

To alter only the effect of the TGFβ1 isoform on airways hyperresponsiveness, an excess of TGFβ1 was introduced into the system via two approaches.

a. First, mice were treated with exogenous TGFβ1 during the antigen exposure. In this experiment, a group of mice (N=3) was treated with 1.0 µg/mouse/day of TGFβ1 for the last 3 days of the OVA exposure which is described in Example 1. The $R_L$ dose-response curves for TGFβ1 treated mice, when compared to untreated controls, were not appreciably different (data not shown). However, the white blood cell counts were considerably lower in TGFβ1 treated mice ($6.5 \times 10^4$ vs. $22 \times 10^4$)

b. Second, untreated (i.e., non-antigen exposed) mice were infected with the Ad5 TGFβ1 adenovirus vector. In this experiment, two groups of otherwise naive mice were treated with either $1 \times 10^8$ pfu of Ad5 DL 70-3 empty (empty control viral vector) or $1 \times 10^8$ pfu of Ad5 TGFβ1 (vector containing TGFβ1 gene). Airways responsiveness was measured in response to inhaled methacholine. There was no apparent change in dose-response relationships between the two groups for inhaled methacholine or lavageable cells (data not shown). Since treatment with the TGFβ1 vector did not increase responsiveness, it is possible that this isoform has an anti-inflammatory effect. These vectors can be used in further studies such as in the antigen-driven airways hyperresponsiveness experiments described in Example 1. It is predicted that in such experiments, mice treated with Ad5 TGFβ1 will show a down-regulated response to antigen exposure.

Example 11

The following example demonstrates that blockade of the TGFβ1 isoform increased airways responsiveness.

Figure 11:
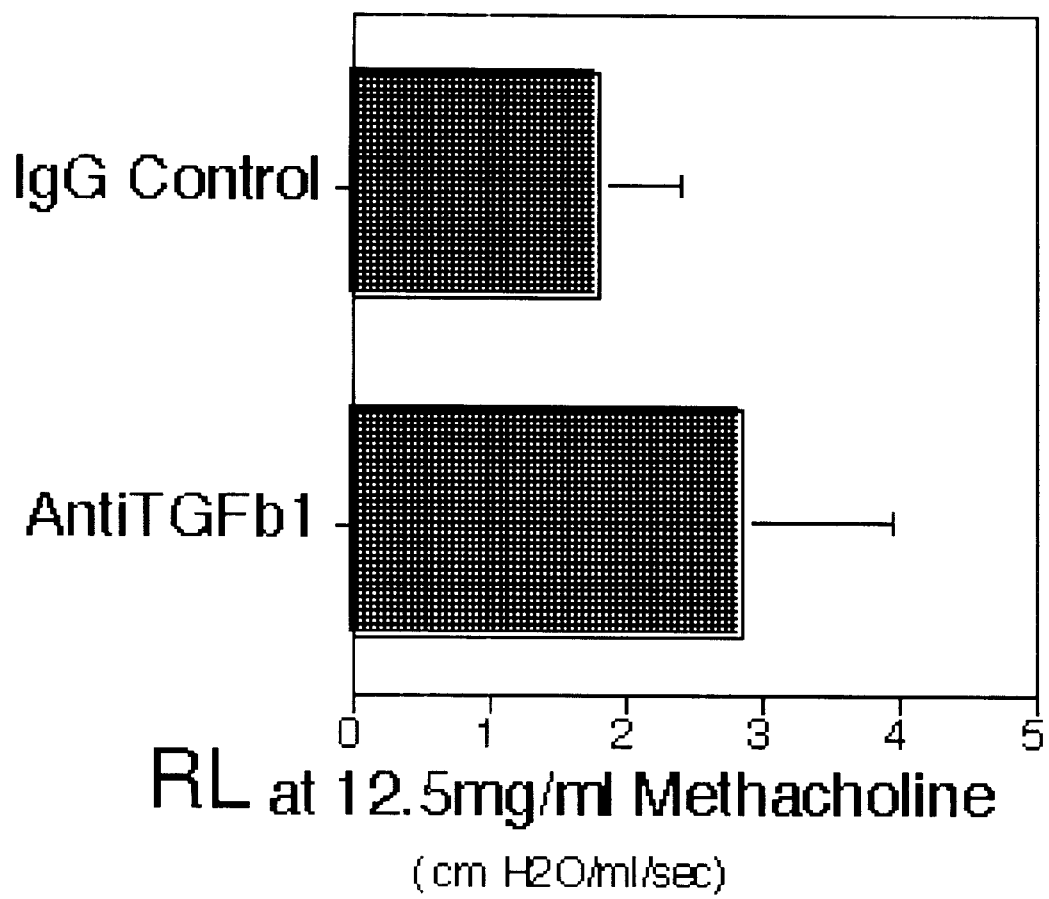
FIG. 11 is a bar graph showing the effect of anti-TGFβ1 antibody on antigen-driven airways hyperresponsiveness.

Given the results shown in the above examples, two groups of animals were studied with the following treatments. One group (N=4) was treated with a neutralizing antibody which is specific against the TGFβ1 isoform. A second group was given chicken IgG (N=3) as an isotype control. Both groups were immunized and OVA challenged as described in Example 1. FIG. 11 shows that administration of anti-TGFβ1 increased the response to 12.5 mg/ml of inhaled methacholine. In addition, treatment with anti-TGFβ1 markedly increased the inflammatory response, as shown in Table 1.

TABLE 1

| Treatment | WBC ($\times 10^4$) | % Eosinophils |
| --- | --- | --- |
| IP, OVA, anti-TGFβ1 | 13.1 ± 2.3* | 33.7 ± 12.0 |
| IP,OVA, IgG | 13.5 ± 2.9 | 3.3 ± 2.6 |
| IP, OVA, no antibody | 12.0 ± 2.1 | 2.0 ± 0.5 |
| Naive controls | 2.0 ± 0.5 | 0.5 ± 0.3 |

*mean ± SEM; N = 3–5 in each group

These data show that treatment with anti-TGFβ1 enhances the response to antigen exposure.

The above results show that 1) exogenous TGFβ1 treatment shows no effect on airway responsiveness and reduces inflammation; 2) endogenous over-expression of the TGFβ1 gene in antigen-naive animals also did not enhance airways responsiveness; and 3) blockade of TGFβ1 markedly enhances the response to antigen. These results indicate that TGFβ1 plays an inhibitory role in airways responsiveness. As such, the pan-specific anti-TGFβ data shown in Example 6 indicate that the TGFβ2 and/or TGFβ3 isoforms increase airways responsiveness.

These results are entirely unexpected, because, for the first time, evidence is provided herein for a differential role for the TGFβ isoforms in airways responsiveness and respiratory inflammatory condition. These results may explain the heretofore contradictory and controversial role proposed for TGFβ in inflammation. Accordingly, further experiments include performing similar experiments as those described in Examples 10 and 11 with TGFβ2 and TGFβ3 isoforms (e.g., antibody experiments and over-expression experiments).

Example 12

The following example demonstrates the role of TGFβ2 and TGFβ3, but not TGFβ1, in causing fibrosis and hyperresponsiveness.

As described in detail in Example 1, BALB/c mice are immunized intraperitoneally with 10 µg OVA in 100 mg Al(OH)$^3$ dissolved in phosphate buffered saline (PBS). The mice are then chronically exposed (i.e., challenged) for 8 days (i.e., 8 exposures of 30 minutes each in 8 days) to 1% aerosolized OVA. To assess the effect of blocking antibodies against each of the three isoforms of TGFβ, seven groups of mice are studied: (1) immunized (IM); (2) immunized and challenged with 8 days of aerosolized antigen (OVA); (3) antibody treated with pre-immune rabbit IgG serum (IgG); (4) immunized and challenged with 8 days of aerosolized antigen plus anti-TGFβ1 (OVA+AbTGF1); (5) immunized and challenged with 8 days of aerosolized antigen plus anti-TGFβ2 (OVA+AbTGF2); (6) immunized and challenged with 8 days of aerosolized antigen plus anti-TGFβ3 (OVA+AbTGF3); and (7) immunized and challenged with 8 days of aerosolized antigen plus pan-specific anti-TGFβ (OVA+AbTGF). Antibody treated animals are administered 25 µg in 25 µl of the neutralizing antibody to TGFβ (β1, β2, β3 or pan-specific), intranasally.

To characterize pulmonary function, measurements of airway resistance ($R_L$) and dynamic compliance ($C_L$) and hyperresponsiveness are obtained as described in Example 1. Results from groups (1), (2), (3), (4) and (7) will be as shown in Example 6. In accordance with the present invention, treatment with anti TGFβ1 antibody is expected to have no effect on airways hyperresponsiveness or actually increase the hyperresponsiveness demonstrated by immunized and challenged mice. Treatment with either of anti-TGFβ2 or anti-TGFβ3 is expected to produce results similar to those for group (7) (i.e., the pan-specific antibody).

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed:

1. A method to reduce airway hyperresponsiveness and/or airflow limitation associated with a respiratory disease involving an inflammatory response in a mammal, comprising administering to the lungs of said mammal a formulation comprising a TGFβ-regulating agent selected from the group consisting of:
   a. an isolated TGFβ1 protein;
   b. an isolated nucleic acid molecule encoding a TGFβ1 protein, wherein said nucleic acid molecule is operatively linked to a transcription control sequence; and,
   c. a TGFβ1 receptor-specific antibody that stimulates the activity of said receptor.

2. The method of claim 1, wherein said TGFβ-regulating agent is a TGFβ1 receptor-specific antibody that stimulates the activity of said receptor.

3. The method of claim 1, wherein said TGFβ-regulating agent is an isolated TGFβ1 protein.

4. The method of claim 1, wherein said TGFβ-regulating agent is an isolated nucleic acid molecule encoding a TGFβ1 protein, wherein said nucleic acid molecule is operatively linked to a transcription control sequence.

5. The method of claim 4, wherein said isolated nucleic acid molecule is administered to said mammal complexed with a liposome delivery vehicle.

6. The method of claim 4, wherein said isolated nucleic acid molecule is administered to said mammal in a viral vector delivery vehicle.

7. The method of claim 6, wherein said viral vector delivery vehicle is from adenovirus.

8. The method of claim 4, wherein said isolated nucleic acid molecule, when administered to the lungs of said mammal, is expressed in cells of said mammal.

9. The method of claim 1, wherein said disease is a chronic obstructive pulmonary disease of the airways associated with eosinophilic inflammation.

10. The method of claim 1, wherein said disease is selected from the group consisting of asthma, occupational asthma and reactive airway disease syndrome.

11. The method of claim 1, wherein administration of said TGFβ-regulating agent reduces airway hyperresponsiveness in said mammal.

12. The method of claim 1, wherein said TGFβ-regulating agent decreases methacholine responsiveness in said mammal.

13. The method of claim 1, wherein said TGFβ-regulating agent decreases airways fibroproliferation in said mammal.

14. The method of claim 1, wherein said TGFβ-regulating agent decreases lung inflammation in said mammal.

15. The method of claim 1, wherein said TGFβ-regulating agent reduces the airflow limitation of a mammal such that the $FEV_1/FVC$ value of said mammal is improved by at least about 5%.

16. The method of claim 1, wherein administration of said TGFβ-regulating agent results in an improvement in a mammal's $PC_{20methacholine}FEV_1$ value such that the $PC_{20methacholine}FEV_1$ value obtained before administration of the TGFβ-regulating agent when the mammal is provoked with a first concentration of methacholine is the same as the $PC_{20methacholine}FEV_1$ value obtained after administration of the TGFβ-regulating agent when the mammal is provoked with double the amount of the first concentration of methacholine.

17. The method of claim 16, wherein said first concentration of methacholine is between about 0.01 mg/ml and about 8 mg/ml.

18. The method of claim 1, wherein said TGFβ-regulating agent is administered in an amount between about 0.1 microgram×kilogram$^{-1}$ and about 10 milligram×kilogram$^{-1}$ body weight of a mammal.

19. The method of claim 1, wherein said TGFβ-regulating agent is administered in a pharmaceutically acceptable excipient.

20. The method of claim 1, wherein said mammal is a human.

21. The method of claim 1, wherein said TGFβ-regulating agent is administered by at least one route selected from the group consisting of nasal and inhaled routes.

22. The method of claim 1, wherein said disease is selected from the group consisting of asthma, allergic bronchopulmonary aspergillosis, hypersensitivity pneumonia, eosinphilic pneumonia, allergic bronchitis bronchiectasis, hypersensitivity pneumotitis, occupational asthma, reactive airway disease syndrome, hypereosinophilic syndrome, rhinitis, sinusitis, and parasitic lung disease.

23. A method for prescribing treatment for airway hyperresponsiveness and/or airflow limitation associated with a respiratory disease involving an inflammatory response in a mammal, comprising:
   a. administering to the lungs of a mammal a TGFβ-regulating agent selected from the group consisting of: a TGFβ1 receptor-specific antibody that stimulates the activity of said receptor an isolated TGFβ1 protein; and an isolated nucleic acid molecule encoding a TGFβ1 protein, wherein said nucleic acid molecule is operatively linked to a transcription control sequence;
   b. measuring a change in lung function in response to a provoking agent in said mammal to determine if said TGFβ-regulating agent modulates airway hyperresponsiveness; and
   c. prescribing a pharmacological therapy comprising administration of TGFβ-regulating agent to said mammal effective to reduce inflammation based upon said changes in lung function.

24. The method of claim 23, wherein said provoking agent is selected from the group consisting of a direct and an indirect stimulus.

25. The method of claim 23, wherein said provoking agent is selected from the group consisting of an allergen, methacholine, a histamine, a leukotriene, saline, hyperventilation, exercise, sulfur dioxide, adenosine, propranolol, cold air, an antigen, bradykinin, acetylcholine, a prostaglandin, ozone, environmental air pollutants and mixtures thereof.

26. The method of claim 23, wherein said step of measuring comprises measuring a value selected from the group consisting of $FEV_1$, $FEV_1/FVC$, $PC_{20methacholine}FEV_1$, post-enhanced pause (Penh), conductance, dynamic compliance, lung resistance ($R_L$), airway pressure time index (APTI), and peak flow.

27. A formulation for protecting a mammal from airway hyperresponsiveness, airflow limitation and/or airway fibrosis associated with a respiratory disease involving inflammation, comprising an anti-inflammatory agent effective for reducing eosinophilic inflammation and a TGFβ-regulating agent selected from the group consisting of: a TGFβ1 receptor-specific antibody that stimulates the activity of said receptor; an isolated TGFβ1 protein; and an isolated nucleic acid molecule encoding a TGFβ1 protein, wherein said nucleic acid molecule is operatively linked to a transcription control sequence.

28. The formulation of claim 27, wherein said formulation comprises a pharmaceutically acceptable excipient.

29. The formulation of claim 27, wherein said formulation comprises a controlled release vehicle selected from the group consisting of biocompatible polymers, other polymeric matrices, capsules, microcapsules, microparticles, bolus preparations, osmotic pumps, diffusion devices, liposomes, lipospheres, viral vectors and transdermal delivery systems.

30. The formulation of claim 27, wherein said TGFβ-regulating agent is an isolated TGFβ1 protein.

31. The formulation of claim 27, wherein said TGFβ-regulating agent is an isolated nucleic acid molecule encoding a TGFβ1 protein, wherein said nucleic acid molecule is operatively linked to a transcription control sequence.

32. The formulation of claim 31, wherein said isolated nucleic acid molecule is complexed with a liposome delivery vehicle.

33. The formulation of claim 31, wherein said isolated nucleic acid molecule in a viral vector delivery vehicle.

34. The formulation of claim 33, wherein said viral vector delivery vehicle is from adenovirus.

35. The formulation of claim 27, wherein said TGFβ-regulating agent is a TGFβ1 receptor-specific antibody that stimulates the activity of said receptor.

36. The formulation of claim 27, wherein said TGFβ-regulating agent is selected from the group consisting of: an isolated TGFβ1 protein and an isolated nucleic acid molecule encoding a TGFβ1 protein, wherein said nucleic acid molecule is operatively linked to a transcription control sequence.

37. The formulation of claim 27, wherein said anti-inflammatory agent is selected from the group consisting of anti-IgE, immunomodulating drugs, leukotriene synthesis inhibitors, leukotriene receptor antagonists, glucocorticosteroids, steroid chemical derivatives, anti-cyclooxygenase agents, beta-adrenergic agonists, methylxanthines, cromones, anti-CD4 reagents, anti-IL-5 reagents, surfactants, cytoxin, and heparin.

38. The formulation of claim 27, wherein said anti-inflammatory agent is selected from the group consisting of leukotriene synthesis inhibitors, leukotriene receptor antagonists, glucocorticosteroids, beta-adrenergic agonists, methylxanthines, and cromones.

* * * * *